United States Patent
Fik et al.

(10) Patent No.: US 11,116,702 B2
(45) Date of Patent: Sep. 14, 2021

(54) DENTAL COMPOSITION

(71) Applicant: DENTSPLY DETREY GMBH, Constance (DE)

(72) Inventors: Christoph Fik, Schonenberg a.d. Thur (CH); Joachim E. Klee, Radolfzell (DE); Christian Scheufler, Engen (DE); Christoph Weber, Constance (DE)

(73) Assignee: DENTSPLY SIRONA Inc., York, PA (US)

( * ) Notice: Subject to any disclaimer, the term of this patent is extended or adjusted under 35 U.S.C. 154(b) by 224 days.

(21) Appl. No.: 16/469,186

(22) PCT Filed: Dec. 12, 2017

(86) PCT No.: PCT/EP2017/082485
§ 371 (c)(1),
(2) Date: Jun. 13, 2019

(87) PCT Pub. No.: WO2018/108948
PCT Pub. Date: Jun. 21, 2018

(65) Prior Publication Data
US 2020/0022884 A1 Jan. 23, 2020

(30) Foreign Application Priority Data
Dec. 14, 2016 (EP) .................................. 16204000

(51) Int. Cl.
| | | |
|---|---|---|
| *A61K 6/88* | (2020.01) | |
| *A61K 6/889* | (2020.01) | |
| *A61C 5/50* | (2017.01) | |
| *A61K 6/72* | (2020.01) | |
| *A61K 6/79* | (2020.01) | |
| *A61C 5/00* | (2017.01) | |
| *C07C 233/20* | (2006.01) | |

(52) U.S. Cl.
CPC ............... *A61K 6/889* (2020.01); *A61C 5/00* (2013.01); *A61C 5/50* (2017.02); *A61K 6/72* (2020.01); *A61K 6/79* (2020.01); *C07C 233/20* (2013.01)

(58) Field of Classification Search
CPC ............. A61C 5/00; A61C 5/50; A61K 6/30; A61K 6/50; A61K 6/72; A61K 6/887; A61K 6/889; C07C 233/20; C08F 220/44
USPC .................... 522/175; 523/109–118
See application file for complete search history.

(56) References Cited

U.S. PATENT DOCUMENTS

| | | | |
|---|---|---|---|
| 3,655,605 A | 4/1972 | Smith | |
| 3,814,717 A | 6/1974 | Wilson | |
| 4,143,018 A | 3/1979 | Crisp | |
| 4,209,434 A | 6/1980 | Crisp | |
| 4,298,738 A | 11/1981 | Lechtken | |
| 4,324,744 A | 4/1982 | Lechtken | |
| 4,360,605 A | 11/1982 | Schmitt | |
| 4,376,835 A | 3/1983 | Schmitt | |
| 4,385,109 A | 5/1983 | Lechtken | |
| 4,437,836 A * | 3/1984 | Schmitz-Josten | C08F 2/50 433/199.1 |
| 4,814,362 A | 3/1989 | Billington | |
| 5,154,762 A | 10/1992 | Mitra | |
| 5,318,929 A | 6/1994 | Jana | |
| 5,360,770 A | 11/1994 | Chadwick | |
| 5,501,727 A | 3/1996 | Wang | |
| 5,502,087 A * | 3/1996 | Tateosian | C08F 279/06 523/115 |
| 5,545,676 A | 8/1996 | Palazzotto | |
| 6,949,678 B2 * | 9/2005 | Kunimoto | C07C 327/30 564/255 |
| 8,497,023 B2 * | 7/2013 | Myung | A61L 27/26 428/423.1 |
| 2004/0079258 A1 | 4/2004 | Hoescheler | |
| 2005/0191567 A1 * | 9/2005 | Kunimoto | C07D 335/16 430/7 |
| 2006/0241205 A1 | 10/2006 | Jia | |

(Continued)

FOREIGN PATENT DOCUMENTS

| | | |
|---|---|---|
| EP | 0173567 A2 | 3/1986 |
| EP | 0969789 A2 | 1/2000 |

(Continued)

OTHER PUBLICATIONS

Glass ionomer cement formulations: I. The preparation of novel fluoroaluminosilicate glasses high in fluorine; Journal of Dental Research Jun. 1979 pp. 1607-1619.
Chemistry of Silanes: Interfaces in Dental Polymers and Composites; J.M. Antonucci; Journal of Research of the National Institute of Standards and Technology, 2005, vol. 110, No. 5; pp. 541-558.
"Cyclopolymerization of N-Alkyl-N-allylacrylamides"; Wakichi Fukuda et al; Polymer Journal; vol. 20 No. 4; Apr. 1, 1988; pp. 337-344.
Tert-Butyl Tert-Butyldimethylsilylglyoxylate: A Useful Conjunctive Reagent; Nicewicz D.A. et al; Org. Synth., 2008, 85; pp. 278-286.
Three-Component Coupling Reactions of Silylglyoxylates, Alkynes, and Aldehydes: A Chemoselective One-Step Glycolate Aldol Construction; Nicewicz D.A.; Journal of American Chemical Society, 2005, 127 (17); pp. 6170-6171.

(Continued)

*Primary Examiner* — Sanza L. McClendon
(74) *Attorney, Agent, or Firm* — Dentsply Sirona Inc.

(57) ABSTRACT

The present invention relates to a dental composition comprising a specific polymerizable compound and a polymerization initiator system. Furthermore, the present invention relates to the specific polymerizable compound as such and its use in a dental composition. The specific polymerizable compound of the present invention has an N-allyl (meth)acrylamide group, which nitrogen atom is substituted with an alkyl or alkenyl group optionally substituted by a group selected from a hydroxyl group, a $C_{1-4}$ alkoxy group, a tertiary amino group and a carboxyl group, wherein 1 to 8 carbon atoms in the main chain of the alkyl or alkenyl group may independently from each other be replaced by a heteroatom selected from an oxygen atom and a sulfur atom.

14 Claims, No Drawings

(56) References Cited

U.S. PATENT DOCUMENTS

| | | | |
|---|---|---|---|
| 2010/0032090 A1* | 2/2010 | Myung | A61L 27/48 156/275.5 |
| 2011/0224324 A1* | 9/2011 | Loccufier | C07C 69/54 522/34 |
| 2013/0261212 A1* | 10/2013 | Myung | A61L 27/56 522/86 |
| 2014/0213661 A1* | 7/2014 | Ward | A61L 27/48 514/772.1 |
| 2016/0075831 A1 | 3/2016 | Alabi | |
| 2018/0289592 A1* | 10/2018 | Klee | A61K 6/30 |
| 2019/0117523 A1* | 4/2019 | Fik | A61K 6/887 |

FOREIGN PATENT DOCUMENTS

| | | | |
|---|---|---|---|
| EP | 2604247 A1 | 6/2013 | |
| WO | 2014040729 A1 | 3/2014 | |
| WO | WO-2018109041 A1 * | 6/2018 | A61K 6/30 |

OTHER PUBLICATIONS

Silyl Glyoxylates. Conception and Realization of Flexible Conjunctive Reagents for Multicomponent Coupling; Boyce G.R. et al.; The Journal of Organic Chemistry; 2012, 77 (10); pp. 4503-4515.

Construction of Cyclopentanol Derivatives via Three-Component Coupling of Silyl Glyoxylates, Acetylides, and Nitroalkenes; Boyce G.R. et al.; Organic Letters; 2012 vol. 14 (2); pp. 652-655.

A Search for new radical sources in photoinitiating systems; El-Roz, M. Et al.; Current Trends in Polymer Science; 2011, vol. 15; pp. 1-13.

International Search Report; PCT/EP3028/082485; dated Mar. 27, 2018; dated Apr. 6, 2018.

International Preliminary Report on Patentability; PCT/EP3028/082485; dated Mar. 27, 2018, dated Apr. 6, 2018.

Written Opinion of the International Searching Authority; PCT/EP3028/082485; dated Mar. 27, 2018; dated Apr. 6, 2018.

Preparation of substituted benzoyltrimethylsilanes by the palladium-catalyzed silylation of substituted benzoyl chlorides with hexamethyldisilane; Yamamoto K. et al.; Tetrahedron Letters, 1980, vol. 21, Issue 17; pp. 1653-1656.

Sequence-Defined Polymers via Orthogonal Allyl Acrylamide Building Blocks; M. Porel et al.; Journal of the American Chemical Society, 2014, 136; pp. 13162-13165.

Synthesis of Heterocycles through a Ruthenium-Catalyzed Tandem Ring-Closing Metathesis/Isomerization/N-Acyliminium Cyclization Sequence; E. Ascic et al.; Angewandte Chemie International Edition, 2011, 50, pp. 5188 to 5191.

* cited by examiner

DENTAL COMPOSITION

FIELD OF THE INVENTION

The present invention relates to a dental composition comprising a specific polymerizable compound and a polymerization initiator system. Furthermore, the present invention relates to the specific polymerizable compound as such and its use in a dental composition. The specific polymerizable compound of the present invention has an N-allyl (meth)acrylamide group, wherein the nitrogen atom is further substituted with an alkyl or alkenyl group optionally substituted with a group selected from a hydroxyl group, a $C_{1-4}$ alkoxy group, a tertiary amino group and a carboxyl group, wherein 1 to 8 carbon atoms in the main chain of the alkyl or alkenyl group may independently from each other be replaced by a heteroatom selected from an oxygen atom and a sulfur atom.

BACKGROUND OF THE INVENTION

Polymerizable dental compositions containing polymerizable compounds are known. Conventionally, polymerizable dental compositions are provided for a broad range of applications and must, therefore, meet diverse requirements. For example, a polymerizable dental composition may be a dental adhesive composition, a bonding agent, a pit and fissure sealant, a dental desensitizing composition, a pulp capping composition, a dental composite, dental glass ionomer cement, a dental cement, a dental root canal sealer composition or a dental infiltrant.

Typically, (meth)acrylates and (meth)acrylamides are used as polymerizable compounds in polymerizable dental compositions. (Meth)acrylates are particularly preferred due to high reactivity in radical polymerizations. The polymerization enthalpy per double bond of methacrylates is in the range of from $-\Delta_R H=30$ to 45 kJ/mol and the polymerization enthalpy per double bond of acrylates is in the range of from $-\Delta_R H=45$ to 60 kJ/mol. In order to provide crosslinking capability, polyfunctional (meth)acrylates such as bis-GMA, were used for dental applications as early as 1962.

However, despite high reactivity, conventional polymerizable compounds are problematic due to a leaching problem, whereby unreacted monomer leaches out from the polymerized dental composition due to an insufficient conversion rate of e.g. below 70%. The leaching problem may give rise to toxicological concerns and or insufficient mechanical properties of the cured dental composition.

Moreover, conventional polymerizable compounds for dental compositions often have a high dynamic viscosity and may require the use of additional components for reducing the viscosity of the dental composition. Typical components for adjusting the dynamic viscosity are reactive diluents and/or solvents. However, such additional components may affect the storage stability and the curing properties, in particular shrinkage, of a dental composition.

Finally, acidic compositions such as dental adhesives or glass ionomers, require water compatible polymerizable compounds having high hydrolysis stability.

Conventional polymerizable compounds typically do not feature in combination high reactivity, low viscosity and hydrolysis stability.

M. Porel et al., Journal of the American Chemical Society, 2014, 136, pages 13162 to 13165, discloses N-allyl acrylamide compounds which nitrogen atom is substituted with $C_{1-4}$ alkyl, 2-dimethylaminoethyl or 2-hydroxyethyl. These compounds are used as starting materials for preparing sequence-defined polymers.

E. Ascic et al., Angewandte Chemie International Edition, 2011, 50, pages 5188 to 5191 discloses N-[1-(hydroxymethyl)-2-methylpropyl]-N-2-propen-1-yl-2-propenamide. This compound is used as a starting material for preparing a bicyclic compound.

US-A 2016/075831 discloses sequence defined polymers and methods of making such polymers by polymerizing monomers including N-allyl-N-tridecylacrylamide and N-allyl-N-(2,5,8,11-tetraoxatridecan-13-yl)acrylamide.

Wakichi Fukuda et al.: "Cyclopolymerization of N-Alkyl-N-allylacrylamides", PolymerJournal, Vol. 20, no. 4, (1988), 337-344 discloses N-octyl-N-allylacrylamide.

SUMMARY OF THE INVENTION

It is an object of the present invention to provide a dental composition comprising a polymerizable compound copolymerizable with conventional (meth)acrylates and (meth)acrylamides, which has a high reactivity, low dynamic viscosity and excellent hydrolysis stability.

According to a first aspect, the present invention provides a dental composition comprising
(a) a polymerizable compound of the following formula (I):

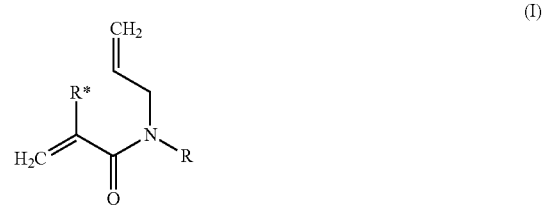

wherein
R represents a straight chain or branched $C_{2-18}$ alkyl or alkenyl group, which may be substituted by a group selected from a hydroxyl group, a $C_{1-4}$alkoxy group, a tertiary amino group, and a carboxyl group, and wherein 1 to 8 carbon atoms in the main chain of the $C_{2-18}$ alkyl or alkenyl group may independently from each other be replaced by a heteroatom selected from an oxygen atom and a sulfur atom, and
R* represents a hydrogen atom or a methyl group; and
(b) a polymerization initiator system.

According to a second aspect, the present invention provides a polymerizable compound of the following formula (I'):

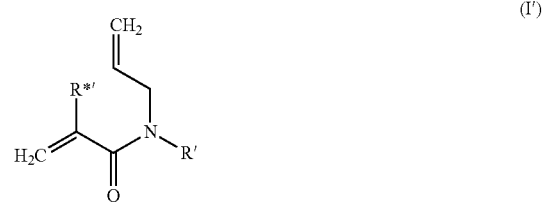

wherein
R' represents a straight chain or branched $C_{5-18}$ alkyl or alkenyl group, which may be substituted by a group selected from a hydroxyl group, a $C_{1-4}$ alkoxy group, a tertiary amino group, and a carboxyl group, and wherein 1 to 8 carbon atoms in the main chain of the $C_{5-18}$ alkyl or alkenyl group may independently from each other be replaced by a heteroatom selected from an oxygen atom and a sulfur atom, and $R^{*'}$ represents a hydrogen atom or a methyl group.

The compound according to formula (I') is preferably other than N-allyl-N-tridecylacrylamide, N-allyl-N-(2,5,8,11-tetraoxatridecan-13-yl)acrylamide or N-octyl-N-allylacrylamide.

According to a third aspect, the present invention provides a use of the above defined polymerizable compound of the following formula (I') in a dental composition.

The present invention is based on the recognition that the polymerizable compound of formula (I) or (I') has low dynamic viscosity of preferably at most 10 Pa·s at 23° C. Accordingly, processing of the compound as such as well as handling of a dental composition comprising the polymerizable compound of formula (I) or (I') are excellent. Furthermore, a polymerizable compound of formula (I) or (I') has high reactivity in terms of polymerization enthalpy $-\Delta_R H$, which is preferably about 50 to 75 kJ/mol. Finally, the polymerizable compound of formula (I) or (I') has an excellent hydrolysis stability.

The combination of low dynamic viscosity, high reactivity and excellent hydrolysis stability allows the polymerizable compounds of formula (I) or (I') to be used as polymerizable compounds without any additional solvents or reactive diluents in a low-viscosity dental composition such as an infiltrant. Moreover, the polymerizable compounds of formula (I) or (I') may be used as reactive diluent(s) for reducing the dynamic viscosity of a high-viscosity dental composition.

DETAILED DESCRIPTION OF PREFERRED EMBODIMENTS

"N-allyl (meth)acrylamide" refers to a (meth)acrylamide group wherein the nitrogen atom of the amide group is substituted by an allyl group.

The term "polymerization" relates to the formation of larger molecules, namely macromolecules or polymers by combining a number of compounds. The term "polymerizable" in the context of a compound refers to the capability of the compound to polymerize under formation of covalent bonds. Polymerizable compounds may form linear macromolecules or they may be combined to form crosslinked polymers having a three-dimensional network structure. Polymerizable compounds having a single polymerizable functional group form linear polymers, whereas polymerizable compounds having at least two polymerizable functional groups may form crosslinked polymers also known as polymer networks.

The term "polymerizable compound" as used herein means a compound having at least one polymerizable double bond, preferably a carbon-carbon double bond. In polymerizable compounds of formulae (I), (III), (IV), (I'), (III') and (IV'), a (meth)acryloyl group and an allyl group contain polymerizable double bonds. The polymerizable compounds of the present invention, which contain at least two polymerizable functional groups are particular in that the formation of cyclic structures reduces the network density.

The term "curing" means the polymerization of polymerizable compounds such as monomers, oligomers or even polymers, into preferably a crosslinked polymer network.

The term "polymerization initiator system" as used herein means any compound or mixture of compounds capable of initiating polymerisation of polymerizable compounds.

The term "infiltrate" refers to a liquid dental composition adapted to infiltrate by readily penetrate into a porous solid such as carious enamel lesions and dentin tubules. After infiltration, the infiltrant may be cured.

The present invention provides a dental composition which is polymerizable or copolymerizable by a polymerization initiator system.

The dental composition may be a dental material to be used in the oral cavity. Preferably, the dental composition according to the present invention is selected from a highly filled dental composite, a flowable dental composite, pit and fissure sealant, a dental adhesive, a dental cement, root canal sealer, a glass ionomer cement and a dental infiltrant.

The Polymerizable Compound (a)

The dental composition of the present invention comprises (a) a polymerizable compound. The dental composition may comprise one or more polymerizable compounds (a). The polymerizable compound (a) is a compound of the following formula (I):

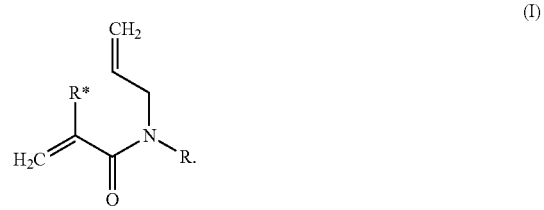

In formula (I), R represents a straight chain or branched $C_{2-18}$ alkyl or alkenyl group, which may be substituted by a group selected from a hydroxyl group, a $C_{1-4}$ alkoxy group, a tertiary amino group, and a carboxyl group, and wherein 1 to 8 carbon atoms in the main chain of the $C_{2-18}$ alkyl or alkenyl group may independently from each other be replaced by a heteroatom selected from an oxygen atom and a sulfur atom. $R^*$ represents a hydrogen atom or a methyl group.

The term "tertiary amino group" in the definition of R of formula (I) means an amino group substituted with two groups which may be the same or different and which are independently selected from $C_{1-4}$ alkyl groups, preferably a methyl group.

It is preferred that R is a group of the following formula (II)

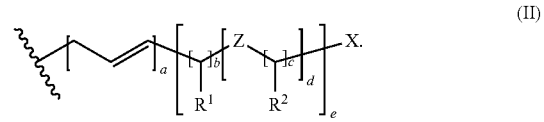

In formula (II), X is a hydrogen atom, a hydroxyl group, a $C_{1-4}$ alkoxy group, a tertiary amino group or a carboxyl group, and Z is an oxygen atom or a sulfur atom, and in case more than one Z is present, the Z may be the same or different. $R^1$ is a hydrogen atom or a group selected from a hydroxyl group, a $C_{1-4}$alkyl group, a $C_{1-4}$alkoxy group, a tertiary amino group, and a carboxyl group. In case more than one group $R^1$ is present, the groups may be the same or different. $R^2$ is a hydrogen atom or a group selected from a hydroxyl group, a $C_{1-4}$ alkyl group, a $C_{1-4}$alkoxy group, a tertiary amino group, and a carboxyl group. In case more than one group $R^2$ is present, the groups may be the same or different.

In formula (II), a is 0 or 1, b is an integer of from 2 to 18, c is an integer of from 2 to 16, d is an integer of from 0 to 8, and e is an integer of from 1 to 3.

If "a" in formula (II) is 1, then R contains a single allylic moiety —[$H_2C$—CH=CH]—, which is attached to the nitrogen atom of the N-allyl (meth)acrylamide group of formula (I), cf. formula (IV) below. If "a" in formula (II) is 0, then R does not contain an allylic moiety.

A compound of formula (II) contains the optional allyl moiety —[$H_2C$—CH=CH]$_a$— and the units —[$CHR^1$]$_b$— and —[Z—[$CHR^2$]$_c$]$_d$. The resulting combination unit —[[$CHR^1$]$_b$—[Z—[$CHR^2$]$_c$]$_d$ may be contained in formula (II) e-fold. In combination unit —[[$CHR^1$]$_b$—[Z—[$CHR^2$]$_c$]$_d$]$_e$, unit —[Z— [$CHR^2$]$_c$]$_d$ is optional, since d may be 0. Therefore, if d is 0, then the substituent X of formula (II) is bound to the terminal position of a chain formed of —[Z—[$CHR^2$]$_c$]$_d$. If d is 1 to 8, then X of formula (II) is bound to the terminal position of a chain formed of —(Z— [$CHR^2$]$_c$]$_d$. It is understood that if d is 0, then a selection for c becomes redundant, because in this case, unit —[Z— [$CHR^2$]$_c$]$_d$ is not contained in formula (II).

For illustration, here are two specific examples for a group of formula (II): If a=0, b=5, d=0, e=1, $R^1$ is a hydrogen atom and X is a hydroxyl group, then formula (II) is n-pentyl-5-ol-$(CH_2)_5$—OH. Or, if a=0, b=5, c=2, d=3, e=1, Z is an oxygen atom, $R^1$ and X respectively represent a hydrogen atom, then formula (II) is n-pentyl-5-tri-ethylene glycol (—$(CH_2)_5$—[O—$CH_2$—$CH_2$]$_3$—OH).

Preferably, in formula (II), a is 0 or 1, b is an integer of from 2 to 12, c is an integer from 2 to 8, d is an integer from 0 to 8, and e is 1 or 2. More preferably, in formula (II), a is 0 or 1, b is an integer of from 2 to 9, c is an integer from 2 to 4, d is an integer from 0 to 2 and 5 to 8, and e is 1 or 2. Most preferably, in formula (II), a is 0 or 1, b is an integer of from 2 to 6, c is 2, d is 0 or an integer of from 5 to 8, and e is 1.

The polymerizable compound of formula (I) may be prepared starting from a N-allyl compound of formula (V) obtained e.g. from a compound of formula (VI), as shown in Scheme 1:

Scheme 1: Preparation of the polymerizable compound of formula (I)

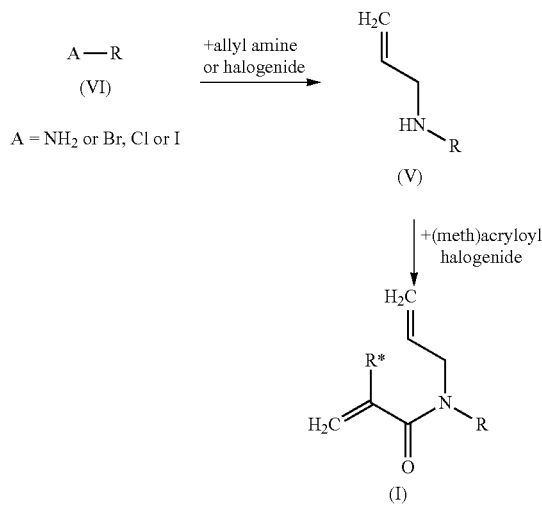

In compounds of formula (VI) and (V), R has the same meaning as defined above for compound of formula (I).

For example, M. Porel et al., Journal of the American Chemical Society, 2014, 136, pages 13162 to 13165, discloses the preparation of N-allyl acrylamide compounds, which nitrogen atom is substituted with $C_{1-4}$ alkyl, 2-dimethylaminoethyl or 2-hydroxyethyl, according to the synthetic pathway shown in Scheme 1 above. This preparation can be applied for the preparation of a polymerizable compound of formula (I).

In case A in the starting compound of formula (VI) is $NH_2$, then an allyl halogenide, preferably a bromide or chloride is applied, while if A is Br, Cl or I, then allyl amine is applied.

The starting compound of formula (VI) can be prepared for example by reacting an alkanol or alkenol derivative selected from the group consisting of $C_{2-18}$alkyl or alkenyl diol, a $C_{2-18}$ alkanol or alkenol, a $C_{1-4}$alkoxy $C_{2-18}$alkanol or alkenol, a tertiary amino $C_{2-18}$ alkanol or alkenol, and a carboxyl $C_{2-18}$alkanol or alkenol with hydroiodic, hydrobromic or hydrochloric acid (HI, HBr, HCl). Thereby, a hydroxyl group of the aforementioned alkanol or alkenol derivative is substituted by an iodine, bromine or chlorine atom.

In compounds of formula (VI) and (V), R may be substituted with a group selected from a hydroxyl group, a $C_{1-4}$alkoxy group, a tertiary amino group, and a carboxyl group. From these groups, in particular hydroxyl and carboxyl groups represent reactive groups which may undesirably react with the allyl halogenide or amine and/or with the (meth)acryloyl halogenide. To avoid such undesired side reactions, the reaction conditions may be suitably set to avoid side reactions of a reactive group such as a hydroxyl or carboxyl group. Alternatively or additionally, the optional reactive group may be protected by a protecting group. In case the optional reactive group is protected, an additional deprotection step may be necessary for converting compound of formula (V) into compound of formula (I).

For the optional reactive group of R of formulae (VI), (V) and (I), the protecting group for e.g. a hydroxyl or carboxyl group is not particularly limited, as long as it is not cleavable under the reaction conditions applied for transferring compound of formula (VI) to the polymerizable compound of formula (I), which are typically basic reaction conditions. For example, the reactive group may be protected by any conventional protecting group, e.g. hydroxyl or carboxyl protecting group described in P. G. M. Wuts and T. W. Greene, Greene's Protective Groups in Organic Synthesis, 4th Edition, John Wiley and Sons Inc., 2007. Particularly preferred protecting groups for a hydroxyl group are e.g. allyl and benzyl ether groups. A particular preferred protecting group for the reactive group representing a carboxyl group is a benzyl ester group. These particular preferred protecting groups can be easily removed by means of hydrogenation in the presence of a suitable catalyst such as platinum or palladium.

It is believed that in a compound of formula (I), the allyl group may take part together with the polymerizable carbon-carbon double bond of the (meth)acryl group in an intramolecular cyclopolymerization reaction according to the following Scheme 2:

Scheme 2: Intramolecular cyclopyolymerization of compound of formula (I)

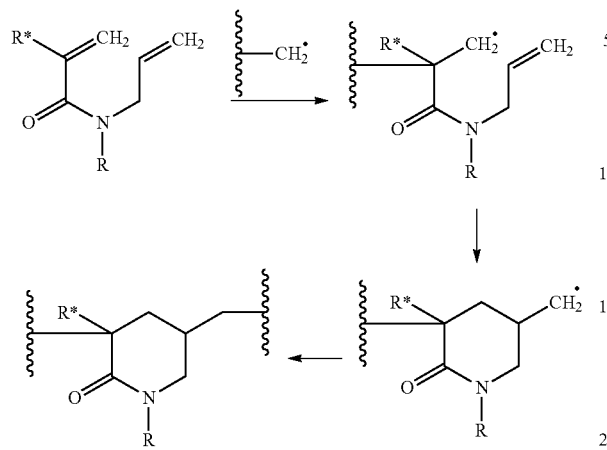

Due to the intramolecular cyclopolymerization, additional reaction enthalpy is gained. Namely, the reactivity of a compound of formula (I) is increased compared to conventional (meth)acrylates lacking an adjacent N-allyl group. Preferably, this intramolecular cyclopolymerization provides for an increased reactivity in terms of a polymerization enthalpy $-\Delta_R H$ of about 50 to 75 kJ/mol. Thereby, a high conversion of preferably at least 70% is attained, whereby the leaching problem is alleviated. Moreover, the network density is reduced due to the intramolecular cyclisation which in turn may reduce polymerisation stress as compared with polymerizable compounds having identical molar mass and an identical number of polymerizable double bonds, but lacking an N-allyl (meth)acrylamide group.

The formation of rings can be demonstrated, for example, by infrared spectroscopy (IR) alone or in combination with a further analytical method, for example nuclear magnetic resonance spectroscopy (NMR).

Preferably, the polymerizable compound of formula (I) is selected from the following structural formulae (III) or (IV):

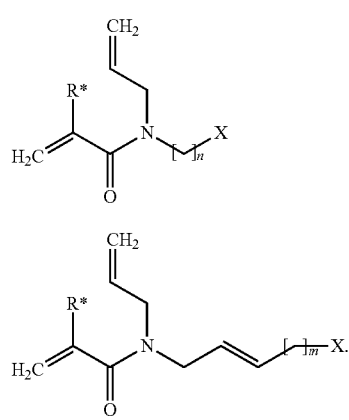

In formulae (III) and (IV), R* represents a hydrogen atom or a methyl group, preferably a hydrogen atom, X is a hydrogen atom, a hydroxyl group, a tertiary amino group or a carboxyl group, n is an integer of from 5 to 18, and m is an integer of from 2 to 15.

Preferably, in the compound of formula (III), n is 6 to 12, and in the compound of the formula (IV), n is 2 to 8.

Compounds of formula (IV) are preferred, since they contain a double bond imparting C—H acidity to the hydrogen atom of the adjacent moiety —CH—N-allyl. Without wishing to be bound to theory, it is believed that this C—H acidity, in combination with the polymerizable C—C double bond of the (meth)acryl group provides for the particularly advantageous polymerization enthalpy and viscosity of compound of formula (IV). In addition, owing to the above described C—H acidity, the compound of formula (IV) may provide an advantageous maximum rate of polymerization and desirable mechanical characteristic such as flexural strength.

Particular preferred compounds of formula (I) have the following structural formulae:

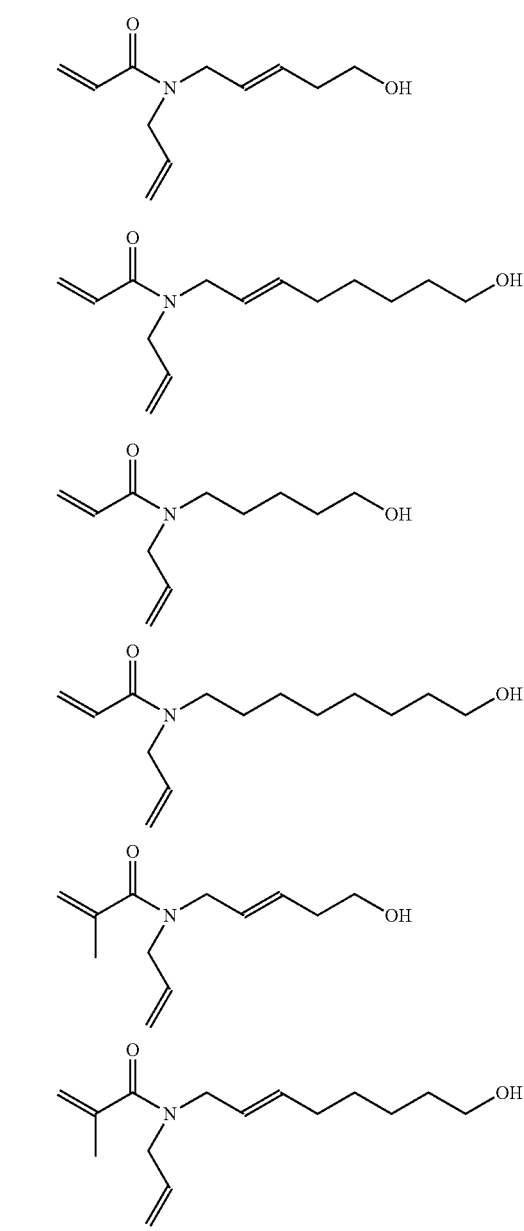

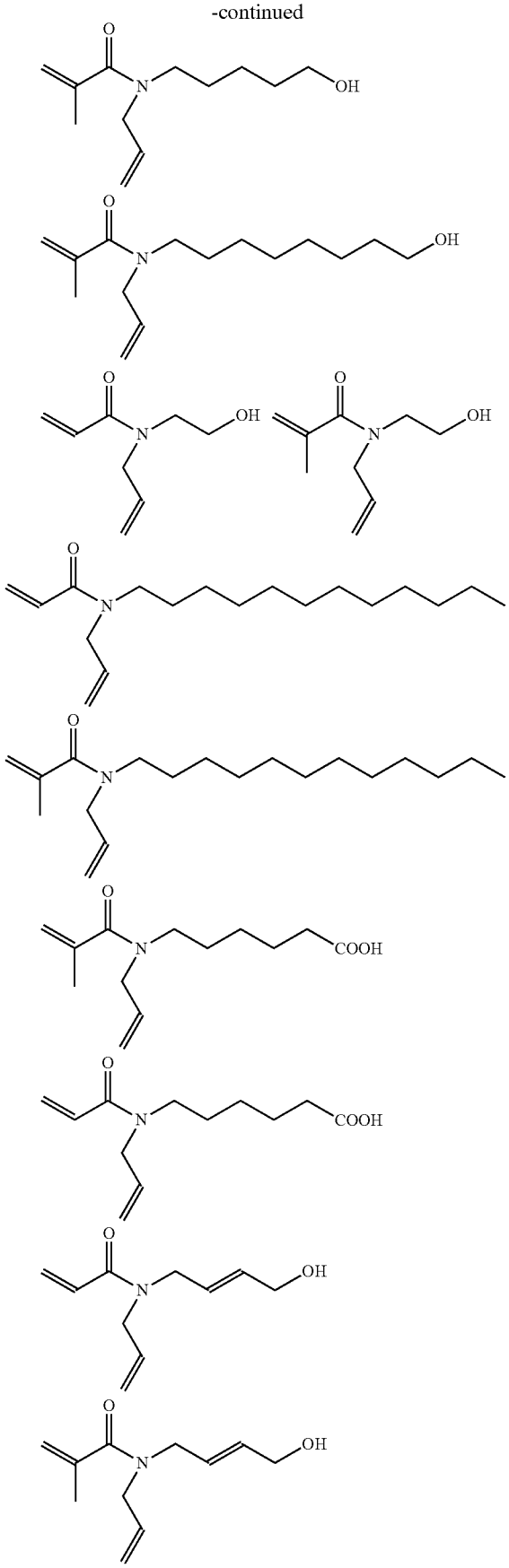
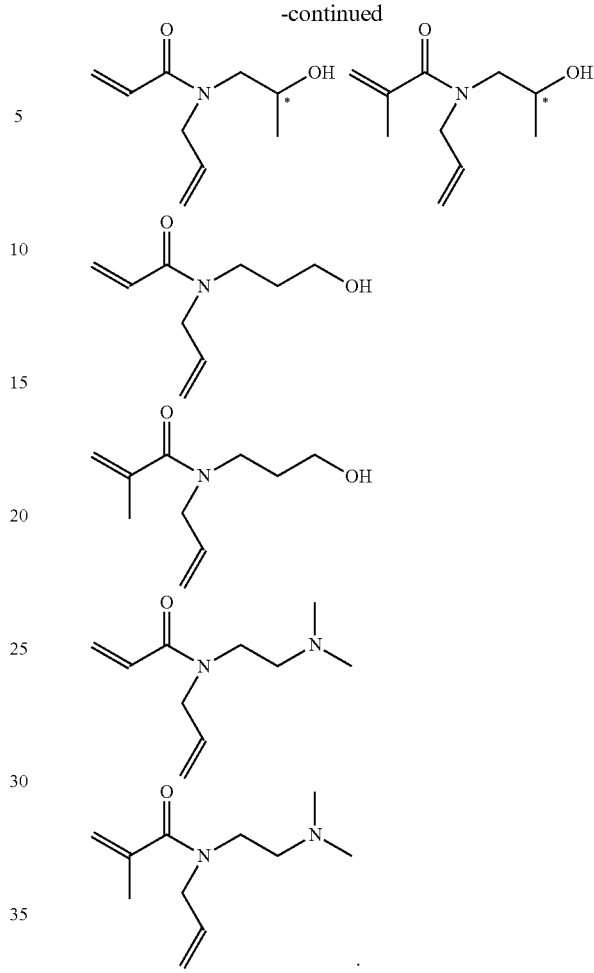

From the particularly preferred polymerizable compounds of formula (I) shown above, the acryloyl compounds are most preferred.

In case R of formula (I) represents a branched and/or substituted alkyl or alkenyl group, R may have one or more chiral centers, that is one or more carbon atoms respectively having four different substituents. For example, the above shown particular preferred compound of formula (I) with R=2-hydroxypropyl has one chiral center, which is indicated with "*" in its structural formula.

From a polymerizable compound of formula (I) having R with one chiral center, two enantiomers exist. Enantiomers represent mirror images of each other that are non-superimposable. From a polymerizable compound of formula (I) having R with two or more chiral centers, enantiomers and/or diasteromers may exist. Diastereomers do not represent mirror images, and they have different physical properties and different chemical reactivity. That is, by suitably selecting an R with one of more chiral centers, for the polymerizable compound of formula (I), the chemical reactivity of its enantiomers or diastereomers and physical properties of its diastereomers may be advantageously set.

For the compounds of formulae (I), (III) and (IV), it is preferred that X is a hydroxyl group or a carboxylic acid group. Such compounds represent interesting reactive components for dental compositions. For example, these compounds may leach glass components in a glass ionomer dental composition.

The dynamic viscosity of the polymerizable compound of formula (I) is preferably at most 10 Pa·s at 23° C.

Preferably, polymerizable compound of formula (I) has a polymerization enthalpy $-\Delta_R H$ of from 50 to 75 kJ/mol.

In the dental composition according to the invention, the polymerizable compound of formula (I) is preferably contained in an amount of at most 95 percent by weight, preferably from 1 to 80 percent by weight, most preferably from 10 to 50 percent by weight based on the total weight of the composition.

Specifically, for dental infiltrants, the polymerizable compound of formula (I) is preferably contained in an amount of at least 50 percent by weight, more preferably 60 to 95 percent by weight, most preferably 65 to 80 percent by weight based on the total weight of the composition.

Owing to the high amount of (a) the polymerizable compound of formula (I), a present dental composition in the form of an infiltrant readily penetrates into carious enamel lesions, and then infiltrates them. Since compounds of formula (I) also have excellent curing properties and an advantageous hydrolysis stability, a dental infiltrant can be provided having both excellent sealing characteristics and a long lifespan.

The Polymerization Initiator System (b)

The dental composition of the present invention comprises (b) a polymerization initiator system. The polymerization initiator system (b) may be any compound or system capable of initiating the polymerization of the polymerizable compound of formula (I) according to the present invention. The polymerization initiator system (b) may be a photoinitiator system, a redox initiator system or a mixture thereof.

The term "photoinitiator" means any chemical compound forming free radicals when activated, e.g. by exposure to light or interaction with a coinitiator in a photochemical process.

The term "redox initiator" means a combination of an oxidizing agent and a reducing agent, and optionally a catalyst such as a metal salt. The redox initiator system provides for a redox reaction in which radicals are formed. These radicals initiate polymerisation of a radically polymerizable compound. Typically, a redox initiator system is activated, that is redox reaction is initiated, by bringing the redox initiator system in contact with water and/or an organic solvent providing for at least partial dissolution of the oxidising agent and the reducing agent. The optional catalyst may be added to accelerate the redox reaction and thus the polymerization of the radically polymerizable compound.

A mixture of a photoinitiator and a redox initiator is a "dual cure initiator system".

For example, a suitable photoinitiator system may be in the form of a binary or ternary system. A binary system may include a photoinitiator and an electron donor compound, and a ternary system may include an iodonium, sulfonium or phosphonium salt, a photoinitiator, and an electron donor compound, as for example described in U.S. Pat. No. 5,545,676.

Suitable photoinitiators for the polymerization initiator system (b) are Norrish type I and Norrish type II photoinitiators.

Suitable Norrish type I photoinitiators are phosphine oxides and Si— or Ge-acyl compounds.

Phosphine oxide photoinitiators may have a functional wavelength range of about 380 nm to about 450 nm, which include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl)phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Si— or Ge-acyl compound photoinitiators preferably have the following formula (X):

$$X^P\text{-}R^P \qquad (X)$$

wherein $X^P$ is a group of the following formula (XI):

$$R^{11}-\underset{\underset{R^{10}}{|}}{\overset{\overset{R^{12}}{|}}{M}}-\overset{O}{\overset{\|}{C}}- \qquad (XI)$$

wherein

M is Si or Ge;

$R^{10}$ represents a substituted or unsubstituted hydrocarbyl or hydrocarbylcarbonyl group;

$R^{11}$ represents a substituted or unsubstituted hydrocarbyl or hydrocarbylcarbonyl group;

$R^{12}$ represents a substituted or unsubstituted hydrocarbyl group; and $R^P$ (i) has the same meaning as $X^P$, whereby the compound of formula (X) may be symmetrical or unsymmetrical; or (ii) is a group of the following formula (XII):

$$-\overset{\overset{}{\|}}{\underset{O}{C}}-Y^P-R^{13} \qquad (XII)$$

wherein $Y^P$ represents a single bond, an oxygen atom or a group NR', wherein R' represents a substituted or unsubstituted hydrocarbyl group;

$R^{13}$ represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or (iii) when M is Si, $R^P$ may be a substituted or unsubstituted hydrocarbyl group.

Photoinitiator compounds of formula (X) represent polymerization initiators which are particularly suitable for dental compositions. Compounds of formula (X) provide a high polymerization efficiency, and coloration problems are avoided. Moreover, in a polymerization system comprising a conventional photoinitiator such as camphor quinone, coloration is efficiently suppressed. Furthermore, compounds of formula (X) have a light absorption within the wavelength range typically applied in dental application, they are compatible with the ingredients of dental compositions and besides, they are considered physiologically harmless. Therefore, compounds of formula (X) are particularly preferred as photoinitiators.

In connection with compound of formula (X), the term "substituted" as used herein means that $R^{10}$, $R^{11}$, $R^{12}$, $R^{13}$ and R' may be substituted by a substituent selected from the group consisting of halogen atoms, a nitro group, a cyano group, a hydroxy group, an amino group, $C_{1-6}$ alkyl groups, $C_{1-6}$ alkoxy groups and a —$NR^xR^y$ group wherein $R^x$ and $R^y$ independently from each other represent a $C_{1-6}$ alkyl group. Here, illustrative of the halogen atoms can be fluorine, chlorine, bromine and iodine. The $C_{1-6}$ alkyl groups are, for example, methyl, ethyl, n-propyl, isopropyl and n-butyl. Illustrative of the $C_{1-6}$ alkoxy groups are, for example, methoxy, ethoxy and propoxy. The alkyl moieties in these substituents may be linear, branched or cyclic. Preferably, the substituent is selected from a chlorine atom, a nitro group, a $C_{1-4}$ alkoxy group and a —$NR^xR^y$ group wherein $R^x$ and $R^y$ independently from each other represent a $C_{1-4}$ alkyl group.

If $R^{10}$, $R^{11}$ and $R^{12}$ are substituted, then it is preferred that they are substituted with 1 to 3 substituents, more preferably with 1 substituent.

In the compound of formula (X), moieties $R^{10}$, $R^{11}$ and $R^{12}$ may be defined as follows:

$R^{10}$ and $R^{11}$ independently from each other represent a substituted or unsubstituted hydrocarbyl or hydrocarbylcarbonyl group, and $R^{12}$ represents a substituted or unsubstituted hydrocarbyl group.

The hydrocarbyl group may be an alkyl group, a cycloalkyl group, a cycloalkylalkyl group, an arylalkyl group or an aryl group.

An alkyl group may be straight-chain or branched $C_{1-20}$ alkyl group, typically a $C_{1-8}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl(-) methylcyclobutyl(-), methylcyclopentyl(-), methylcyclohexyl(-), ethylcyclopropyl(-), ethylcyclobutyl(-), ethylcyclopentyl(-), ethylcyclohexyl(-), propylcyclopropyl(-), propylcyclobutyl(-), propylcyclopentyl(-), propylcyclohexyl(-).

An arylalkyl(-) group may be a $C_{7-20}$ arylalkyl(-) group, typically a combination of a linear or branched alkyl group having 1 to 6 carbon atoms and an aryl(-) group having 6 to 10 carbon atoms. Specific examples of an arylalkyl(-) group are a benzyl(-) group or a phenylethyl(-) group.

An aryl group can include aryl groups having 6 to 10 carbon atoms. Examples of the aryl group are phenyl and naphtyl.

The hydrocarbylcarbonyl groups of $R^{10}$ and $R^{11}$ represent acyl groups ($R_{org}$-(C=O)—) in which the organic residue $R_{org}$ is a hydrocarbyl residue as defined above.

Compound of formula (X) may contain one or two hydrocarbylcarbonyl groups, that is either one of $R^{10}$ or $R^{11}$ is a hydrocarbylcarbonyl group, or both $R^{10}$ and $R^{11}$ are hydrocarbylcarbonyl groups. Preferably, compound of formula (X) contains one hydrocarbylcarbonyl group.

Preferably, the hydrocarbylcarbonyl group is an arylcarbonyl group, more preferably a benzoyl group.

Preferably, $R^{10}$ and $R^{11}$ are independently selected from the group consisting of a straight chain or branched $C_{1-6}$ alkyl group, and a phenyl or benzoyl group which may optionally be substituted by one to three substituents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^{12}$ is a straight chain or branched $C_{1-5}$ alkyl group or a phenyl group.

Most preferably, $R^{10}$ and $R^{11}$ are independently selected from the group consisting of a straight chain or branched $C_{1-4}$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_{1-4}$ alkyl group, and $R^{12}$ is a straight chain or branched $C_{1-4}$ alkyl group.

In the compound of formula (X), $R^P$ may have the same meaning as $X^P$, whereby the compound of formula (X) may be symmetrical or unsymmetrical. Alternatively, $R^P$ may represent a substituted or unsubstituted hydrocarbyl group, or a group of formula (XII). Preferably, if $R^P$ has the same meaning as $X^P$, then compound of formula (X) is unsymmetrical. If $R^P$ represents a substituted or unsubstituted hydrocarbyl group, then the hydrocarbyl group has the same meaning as defined above for $R^6$ and is independently selected therefrom.

In the group of formula (XII) of compound of formula (X), $R^{13}$ represents a substituted or unsubstituted hydrocarbyl group, a trihydrocarbylsilyl group, a mono(hydrocarbylcarbonyl)-dihydrocarbylsilyl group or a di(hydrocarbylcarbonyl)monohydrocarbylsilyl group.

If $R^{13}$ of formula (XII) is a trihydrocarbylsilylgroup, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^{10}$, $R^{11}$ and $R^{12}$ and is independently selected therefrom.

In formula (XII), R' has the same meaning as defined for $R^{12}$ and is independently selected therefrom.

If M is Si in compound of formula (X), $R^P$ may be also be a substituted or unsubstituted hydrocarbyl group, wherein the hydrocarbyl group has the same meaning as defined above for $R^{12}$ and is independently selected therefrom.

For example, compounds of formula (X) wherein $R^P$ has the same meaning as $X^P$ and which are symmetrical may be have the following structural formulae:

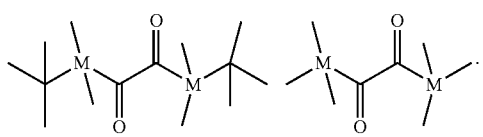

For example, compounds of formula (X) wherein $R^P$ represents a group of formula (XII) wherein $Y^P$ is a bond, an oxygen atom or a NR' group, and $R^{13}$ represents a substituted or unsubstituted hydrocarbyl group may have the following structural formulae:

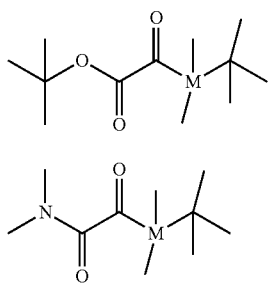

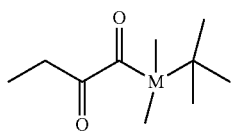

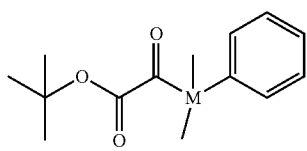

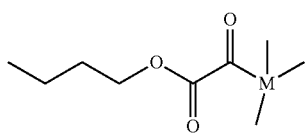

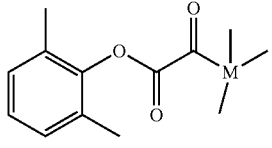

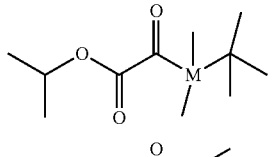

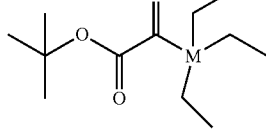

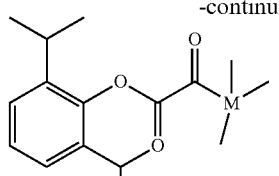

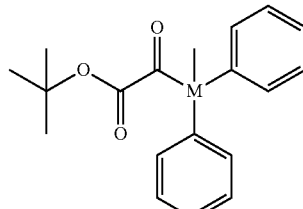

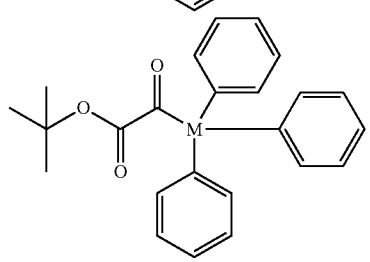

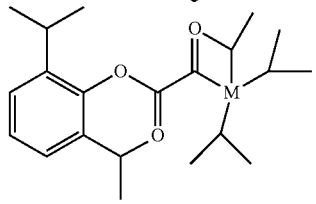

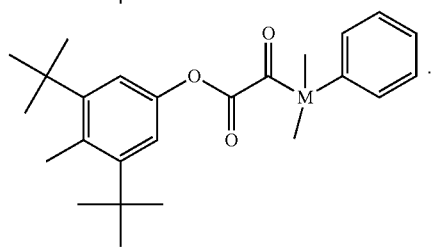

For example, compounds of formula (X) wherein $R^P$ represents a group of formula (XII) wherein $R^{13}$ represents a trihydrocarbylsilyl group have the following structural formulae:

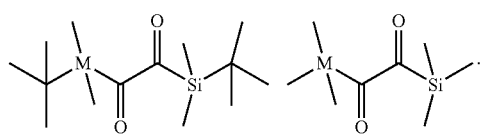

For example, compounds of formula (X) wherein M is Si and $R^P$ represents a substituted or unsubstituted hydrocarbyl group, may have the following structural formulae:

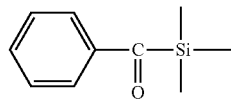

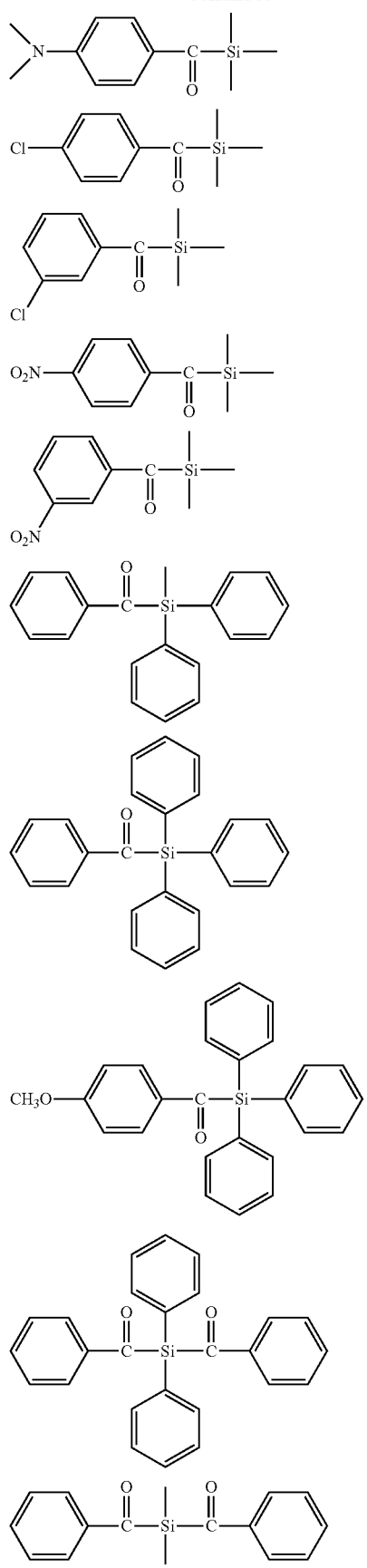
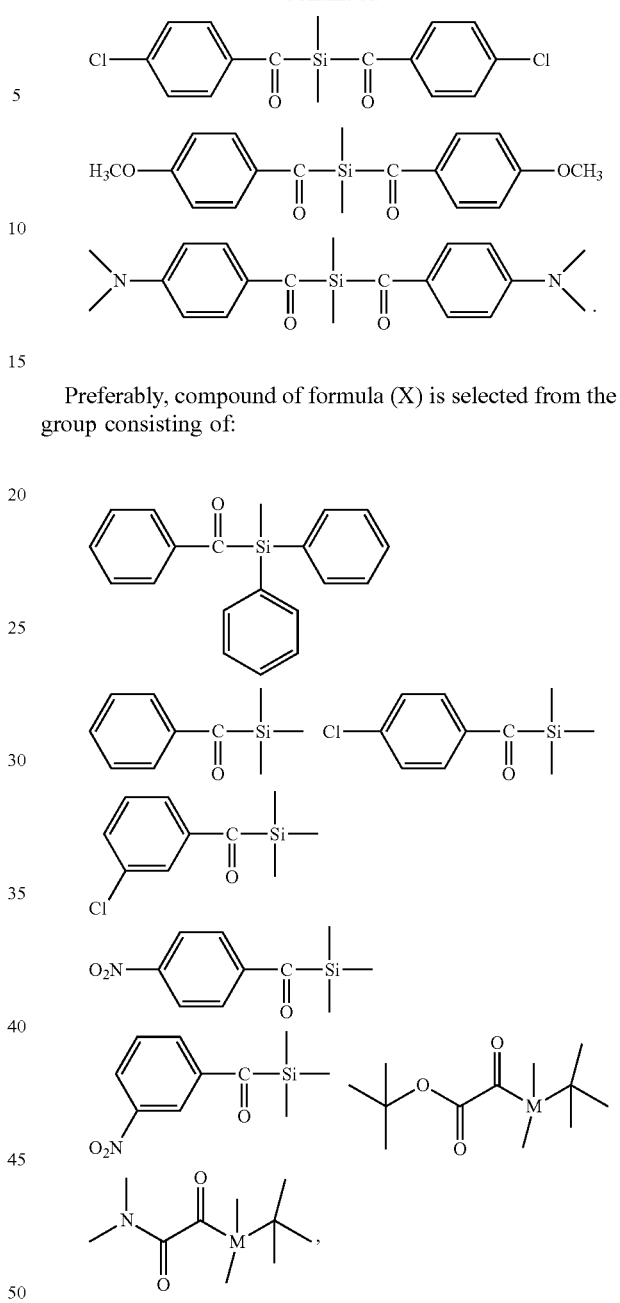
Preferably, compound of formula (X) is selected from the group consisting of:
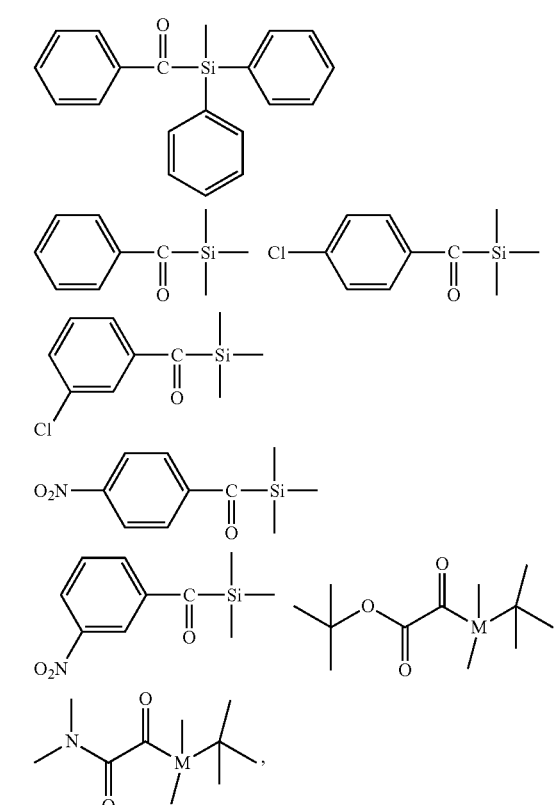
wherein compounds of formula (X) with M=Si are particularly preferred.
Most preferably, compound of formula (X) is selected from the group consisting of: compound of formula (X) is selected from the group consisting of:
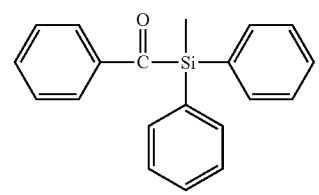

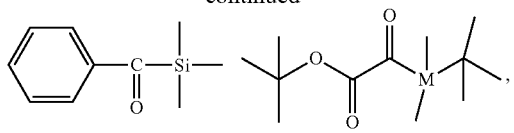

wherein it is particularly preferred that M=Si.

Suitable Norrish type II photoinitiators are for example combinations of sensitizer compounds such as monoketones and diketones that absorb some light within a range of about 400 nm to about 520 nm (preferably, about 450 nm to about 500 nm) with a coinitiator. Particularly suitable sensitizer compounds include alpha diketones that have some light absorption within a range of about 400 nm to about 520 nm (even more preferably, about 450 to about 500 nm). Examples of sensitizer compounds include camphor quinone, benzil, furil, 3,3,6,6-tetramethylcyclo-hexanedione, phenanthraquinone, 1-phenyl-1,2-propanedione and other 1-aryl-2-alkyl-1,2-ethanediones, and cyclic alpha diketones. Suitable coinitiators are electron donor compounds including substituted amines, e.g., ethyl dimethylaminobenzoate or dimethylamino benzonitrile, or a polymerizable compound having CH-acidity such as the present polymerizable compounds of formula (IV).

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylaminobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

In case the dental composition is in the form of an acidic composition, that is a composition having a pH of less than 7, depending on the composition's pH level, it is preferred to select compounds of formula (X) with the proviso that they do not contain ester groups, or at least only ester groups which do not significantly hydrolyse in aqueous media at pH 3 at room temperature within one month. Thereby, an advantageous stability of an acidic dental composition, that is a composition having a pH of less than 7, in terms of shelf-life stability of the uncured dental composition as well as stability after curing in the mouth of a patient is ensured. Therefore, for acidic dental compositions, particularly preferred are compounds of formula (X) excluding $R^P$ being a group of formula (XII) in which $Y^P$ is an oxygen atom.

Furthermore, since the acylsilyl moiety (—C(=O)—Si—) might be sensitive to basic conditions, that is a pH higher than 7, it is preferred to suitably select a pH value of the composition being higher than 7 with the proviso that the acylsilyl moiety is not cleaved in aqueous media at the selected basic pH at room temperature within one month.

The compound of the formula (X) may be a known compound which is commercially available or a may be prepared according to published procedures.

The compound of formula (X) wherein M is Si and $R^P$ represents a substituted or unsubstituted hydrocarbyl group may for example be readily prepared by means of a one-step Pd-catalyzed reaction with a disilane as described e.g. by Yamamoto K. et al., *J. Tetrahedron Lett.*, 1980, vol. 21, pages 1653 to 1656:

Scheme 3: Preparation of acylsilanes

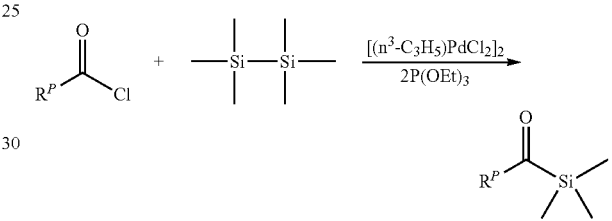

In Scheme 3, the reaction is exemplary depicted with hexamethylsilan as the disilane, whereby a compound of formula (X) wherein $R_{10}$, $R^{11}$ and $R_{12}$ represent a methyl group is obtained. It is understood that $R^{10}$, $R^{11}$ and $R^{12}$ can be varied by applying disilanes having hydrocarbon substituents other than methyl.

The compound of formula (X) wherein $R^P$ represents a group of formula (XII) in which $Y^P$ is an oxygen atom and $R^{13}$ represents a hydrocarbyl group may for example be prepared by a three-step synthesis as described by Nicewicz D. A. et al. in *Org. Synth.*, 2008, 85, pages 278 to 286. In this three-step synthesis, an acetoacetate is converted to an azide compound, which is then reacted with a trihydrocarbylsilyl-trifluoromethane-sulfonate to obtain a trihydrocarbylsilyldiazoacetate, which is finally reacted with potassium peroxymonosulfate to arrive at the target compound:

Scheme 4: Preparation of silylglyoxylates

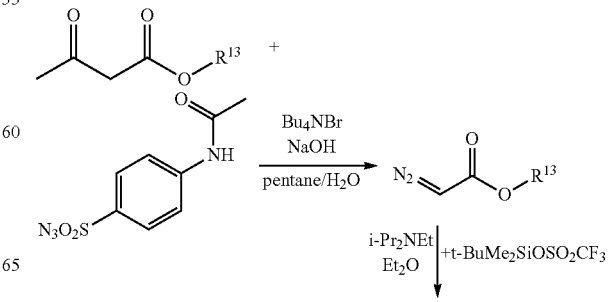

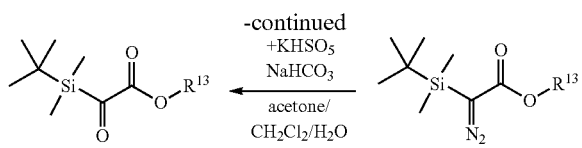

In Scheme 4, the reaction is exemplary depicted for obtaining a compound of formula (X) wherein in $X^P$ of formula (X), $R^{10}$ and $R^{11}$ represent a methyl group, and $R^{12}$ represents a tert-butyl group. It is understood that $R^{10}$, $R^{11}$ and $R^{12}$ can be varied by applying a trihydrocarbylsilyltrifluoromethane-sulfonate other than t-BuMeSiOSO$_2$CF$_3$.

Alternatively, compounds of formula (X) wherein M is Si, $R^P$ represents a group of formula (XII) and $Y^P$ represents an oxygen atom may be prepared by a single-pot three-component coupling reaction of a silylglyoxylate, a terminal alkyne and an aldehyde in the presence of ZnI$_2$ and Et$_3$N as described by Nicewicz D. A. in J. Am. Chem. Soc., 2005, 127 (17), pages 6170 to 6171. Further syntheses of silylglyoxylate compounds are described e.g. by Boyce G. R. et al. in *J. Org. Chem.*, 2012, 77 (10), pages 4503 to 4515 and Boyce G. R. et al. in Org. Lett., 2012, 14 (2), pages 652 to 655.

For example, the following compounds of formula (X) are known and commercially available, and their Chemical Abstracts (CAS) No. is given in brackets benzoyltriphenylsilane (1171-49-9), benzoyltrimethylsilan (5908-41-8), 1-[(trimethylsilyl) carbonyl]-naphthalene (88313-80-8), 1-methoxy-2-[(trimethylsilyl)-carbonyl]-benzene (107325-71-3), (4-chlorobenzoyl) (triphenyl) silane (1172-90-3), (4-nitrobenzoyl) (triphenyl) silane (1176-24-5), (methyldiphenylsilyl)phenyl-methanone (18666-54-1). (4-methoxybenzoyl) triphenylsilan (1174-56-7) and tert-butyl (tert-butyldimethylsilyl)glyoxylate (852447-17-7).

All compounds of formula (X) comprise the group of formula (XI)

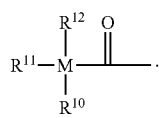

(XI)

In formula (XI), M, $R^{10}$, $R^{11}$ and $R^{12}$ are defined as above. Depending on the selection of M, the group of formula (XI) represents an acylsilane or acylgermane group. Upon exposure to UV-VIS-light, the bond between M and the acyl group may be cleaved, whereby a silyl/germanyl and an acyl radical is formed as a polymerization initiating structure, but in competition to the cleavage into to radicals, a carbene structure might be formed:

Scheme 5: Carbene formation versus radical formation

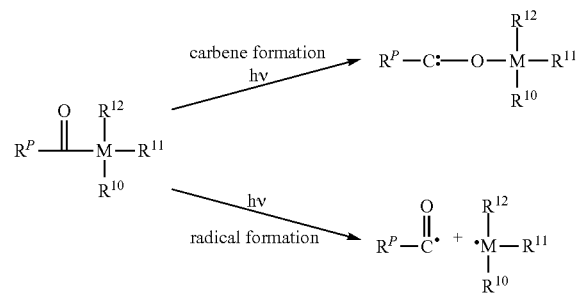

This competition between the formation of polymerization initiating radicals and carbene formation is described for acylsilanes by El-Roz, M. et al. in Current Trends in Polymer Science, 2011, vol. 15, pages 1 to 13.

Besides, in case in compound of formula (X) wherein $R^P$ has the same meaning as $X^P$ or is a group of formula (XII), the C—C bond of the 1,2-diketone moiety (—C(=O)—C(=O)—) may be cleaved upon exposure to UV-VIS-light into two acyl radicals. This cleavage is exemplary shown for compound of formula (X) wherein $R^P$ is a group of formula (XII) and $Y^P$ is an oxygen atom, that is for a glyoxylate (—O—C=O)—C(=O)—) compound:

Scheme 6: Cleavage of —O—C(=O)—C(=O)— moiety of a glyoxylate

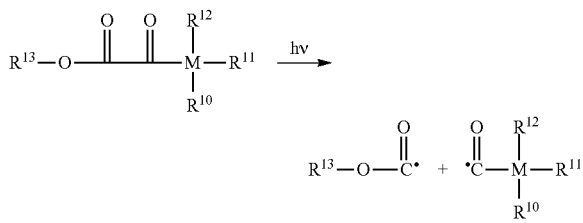

Besides, in compound of formula (X), there is a third possibility for a radical cleavage in case $R^P$ is a compound of formula (XII) wherein $Y^P$ is an oxygen atom and $R^{13}$ is a substituted or unsubstituted hydrocarbyl group. Namely, an intra- or intermolecular hydrogen abstraction might occur, where a hydrogen radical is abstracted:

Scheme 7: Hydrogen abstraction (intra- or intermolecular)

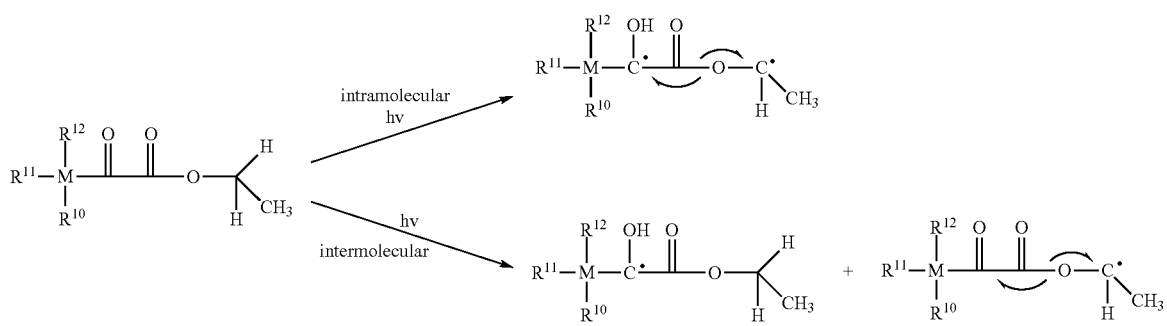

Both the cleavage of a glyoxylate group and the hydrogen abstraction mechanism is known for photoinitiators which do not contain silicium or germanium, such as ethyl phenylglyoxylate (Irgacure® MBF).

For compounds of formula (X) wherein $R^P$ has the same meaning as $X^P$ or is a group of formula (XII), the present inventors carried out molecular modelling calculations from which it appears that a Si—C or Ge—C bond cleavage can be ruled out, since the C—C bond of the —C(=O)—C(=O)— moiety is weaker than the Si—C or Ge—C bond.

The photoinitiator system may further comprise diaryl iodonium salts, triaryl sulfonium salts and tetraaryl or tetraalkyl phosphonium salts. These salts may serve as a coinitiator for improving the polymerization performance of the photoinitiator, but they may also serve as an initiator for cationic polymerization.

For example, diaryl iodonium salt may be selected from the group consisting of (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl) iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl) iodonium hexafluorophosphate, di(3-methoxycarbonylphenyl)iodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methyl phenyl)[4-(2-methylpropyl) phenyl] iodonium tetrafluoroborate, 4-octyloxyphenyl phenyl iodonium hexafluoroantimonate, 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl) borate.

A preferred triaryl sulfonium salt is S-(phenyl)thianthrenium hexafluorophosphate of the following formula:

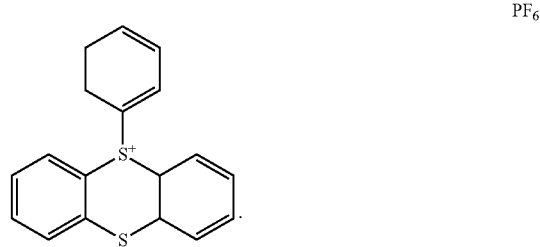 [SMILES: C1=CCCC([S+]2c3ccccc3SC3C=CC=CC32)=C1]

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

A particularly preferred photoinitiator system comprises a photoinitiators of formula (X), optionally in addition with camphor quinone, in combination with a diaryl iodonium salt, triaryl sulfonium salt or a tetraaryl or tetraalkyl phosphonium salt as described above.

A suitable redox initiator system comprises reducing and oxidizing agents, which produce free-radicals capable of initiating polymerization of the polymerizable group(s) of (a) the polymerizable compound of formula (I) or (c) further polymerizable compound(s) independent from the presence of light. The reducing and oxidizing agents are selected so that the polymerization initiator system (b) is sufficiently storage-stable and free of undesirable colorization to permit storage and use under typical dental conditions. Moreover, the reducing and oxidizing agents are selected so that the polymerization initiator system (b) is sufficiently miscible with the resin system to permit dissolution of the polymerization initiator system in the composition.

Useful reducing agents include ascorbic acid, ascorbic acid derivatives, and metal complexed ascorbic acid compounds as described in U.S. Pat. No. 5,501,727; amines, namely tertiary amines, such as 4-tert-butyl dimethylaniline; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine, salts of a dithionite or sulfite anion, and mixtures thereof.

Suitable oxidizing agents include persulfuric acid and salts thereof, such as ammonium, sodium, potassium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof. One or more different oxidizing agents or one or more different reducing agent may be used in the initiator system. Small quantities of transition metal compounds may also be added to accelerate the rate of redox cure. The reducing and oxidizing agents are present in amounts sufficient to permit an adequate free-radical reaction rate.

The reducing or oxidizing agents may be microencapsulated for enhancing shelf stability of the composition, and if necessary permitting packaging the reducing and oxidizing agents together (U.S. Pat. No. 5,154,762). Appropriate selection of an encapsulant may allow combination of the oxidizing and reducing agents and even of an acid-functional component and optional filler in a storage-stable state. Moreover, appropriate selection of a water-insoluble encapsulant allows combination of the reducing and oxidizing agents with the particulate reactive glass and water in a storage-stable state.

Preferably, the polymerization initiator is contained in an amount of from 0.01 to 10 percent based on the total weight of the composition.

Further Polymerizable Compounds (c)

The dental composition of the present invention may optionally comprise (c) a further polymerizable compound besides of (a) the polymerizable compound of formula (I). The dental composition may comprise one or more further polymerizable compound(s) (c).

The term "further polymerizable compound" as used herein encompasses monomers, oligomers and polymers.

The further polymerizable compound (c) is not particularly limited concerning its polymerizable groups. The further polymerizable compound (c) may have one or more polymerizable groups. At least one polymerizable group may for example be a polymerizable carbon-carbon double bond, which may be selected from (meth)acryloyl group(s) and a (meth)acrylamide group(s), preferably (meth)acryloyl group(s).

Suitable examples for a further polymerizable compound (c) in the form of a monomer may be selected from the group consisting of (meth)acrylates, amides of acrylic or methacrylic acid, urethane acrylates or methacrylates, and polyol acrylates or methacrylates.

(Meth)acrylates may be preferably selected from compounds of the following formulae (A), (B) and (C):

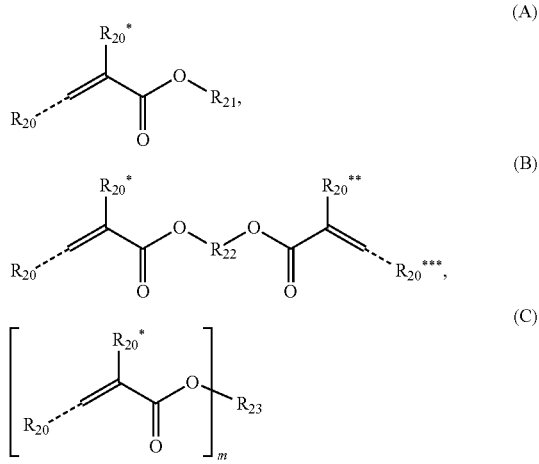

wherein $R_{20}$, $R^*_{20}$, $R^{}_{20}$, $R^{*20}$ independently represent a hydrogen atom, —COOM, a linear $C_{1-18}$ or branched $C_{3-18}$ alkyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, or a $C_5$ to $C_{18}$ aryl or $C_3$ to $C_{18}$ heteroaryl group, —COOM, —PO$_3$M, —O—PO$_3$M$_2$ or —SO$_3$M*, $R_{21}$ represents a hydrogen atom, a linear $C_{1-18}$ or branched $C_{3-18}$ alkyl group or $C_2$ to $C_{18}$ alkenyl group which may be substituted by a $C_{3-6}$ cycloalkyl group, a $C_{6-14}$ aryl or $C_{3-14}$ heteroaryl group, —COOM, —PO$_3$M, —O—PO$_3$M$_2$ or —SO$_3$M*, a $C_3$ to $C_{18}$ cycloalkyl group which may be substituted by a $C_{1-16}$ alkyl group, a $C_{6-14}$ aryl or $C_{3-14}$ heteroaryl group, —COOM, —PO$_3$M, —O—PO$_3$M$_2$ or —SO$_3$M*, or a $C_5$ to $C_{18}$ aryl or $C_3$ to $C_{18}$ heteroaryl group, $R_{22}$ represents a divalent organic residue having from 1 to 45 carbon atoms, whereby the divalent organic residue may contain at least one of from 1 to 7 $C_{3-12}$ cycloalkylene group(s), 1 to 7 $C_{6-14}$ arylene groups, 1 to 7 carbonyl groups, 1 to 7 carboxyl groups (—(C═O)—O— or —O— (C═O—), 1 to 7 amide groups (—(C═O)—NH— or —NH—(C═O)—) or 1 to 7 urethane groups (—NH—(C═O)—O— or —O—(C═O)—NH—), and 1 to 14 heteroatoms selected from oxygen, nitrogen and sulphur, which divalent organic residue may be substituted with one or more substituents selected from the group consisting of a hydroxyl group, a thiol group, a $C_{6-14}$ aryl group, —COOM, —PO$_3$M, —O—PO$_3$M$_2$ or —SO$_3$M*; preferably $R_{22}$ is a $C_1$ to $C_{18}$ alkylene group or a $C_2$ to $C_{18}$ alkenylene group, which may be substituted by one or more —OH group(s), which alkylene or alkenylene group may contain at least one of 1 to 4 $C_{6-10}$ arylene groups, 1 to 4 urethane groups (—NH—(C═O)—O— or —O—(C═O)—NH—), and 1 to 8 oxygen atoms; $R_{23}$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and m is an integer, preferably in the range from 1 to 10, wherein M of any one of $R_{20}$, $R^*_{20}$, $R^{}_{20}$, $R^{*}_{20}$, $R_{21}$, and $R_{22}$, which M are independent from each other, each represent a hydrogen atom or a metal atom, and M* of any one of $R_{20}$, $R^*_{20}$, $R^{}_{20}$, $R^{*}_{20}$, $R_{21}$, and $R_{22}$, which M are independent from each other, each represent a metal atom.

For $R_{20}$, $R^*_{20}$, $R^{}_{20}$ and $R^{*}_{20}$, the linear $C_{1-18}$ or branched $C_{3-18}$ alkyl group may e.g. be methyl, ethyl, n-propyl, i-propyl, n-butyl, isobutyl, tert-butyl, sec-butyl, pentyl or hexyl. For $R_{21}$, and $R^*_{21}$, the $C_{1-18}$ alkyl group or $C_{2-18}$ alkenyl group may e.g. be eth(en)yl, n-prop(en)yl, i-prop(en)yl, n-but(en)yl, isobut(en)yl, tert-but(en)yl sec-but(en)yl, pent(en)yl or hex(en)yl.

For $R_{20}$, $R^*_{20}$, $R^{}_{20}$, $R^{*}_{20}$ and $R_{21}$ an aryl group may, for example, be a phenyl group or a naphthyl group, and a $C_{3-14}$ heteroaryl group may contain 1 to 3 heteroatoms selected from nitrogen, oxygen and sulfur.

For $R_{22}$, in the phrase "divalent organic residue may contain at least one of . . . " means that the groups which may be contained in the divalent organic residue are incorporated in the divalent organic residue by means of covalent bonding. For example, in BisGMA, two aryl groups in the form of phenyl and two heteroatoms in the form of oxygen are incorporated into the divalent organic residue of $R_{22}$. Or, as a further example, in UDMA, two urethane groups (—NH—(C═O)—O— or —O—(C═O)—NH—) are incorporated in the divalent organic residue of $R_{22}$.

In formula (B), the dotted bond indicates that $R_{20}$ and $R^{***}_{20}$ may be in (Z) or (E) configuration relative to CO.

Preferably, in formulae (A), (B) and (C), $R_{20}$, $R^*_{20}$, $R^{}_{20}$ and $R^{*}_{20}$ independently represent a hydrogen atom, a linear $C_{1-16}$ or branched $C_{3-16}$ alkyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, in formula (B), $R_{20}$, $R^*_{20}$, $R^{}_{20}$ and $R^{*}_{20}$ independently represent a hydrogen atom, a linear $C_{1-8}$ or branched $C_{3-8}$ alkyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{20}$, $R^*_{20}$, $R^{}_{20}$ and $R^{*}_{20}$ independently represent a hydrogen atom, a linear $C_{1-4}$ or branched $C_3$ or $C_4$ alkyl group which may be substituted by a cyclohexyl group or a phenyl group, or a cyclohexyl group which may be substituted by a $C_{1-4}$ alkyl group. Most preferably, $R_{20}$, $R^*_{20}$, $R^{}_{20}$ and $R^{*}_{20}$ independently represent a hydrogen atom or a linear $C_{1-4}$ or branched $C_3$ or $C_4$ alkyl group.

Preferably, in formula (A), $R_{21}$ represents a hydrogen atom, a linear $C_{1-16}$ or branched $C_{3-16}$ alkyl group or $C_{2-16}$ alkenyl group which may be substituted by a $C_{3-6}$ cycloalkyl group, a $C_{6-14}$ aryl or $C_{3-14}$ heteroaryl group, a $C_{3-6}$ cycloalkyl group which may be substituted by a $C_{1-16}$ alkyl group, a $C_{6-14}$ aryl or $C_{3-14}$ heteroaryl group, a $C_{6-14}$ aryl or $C_{3-14}$ heteroaryl group. More preferably, $R_{21}$ represents a hydrogen atom, a linear $C_{1-10}$ or branched $C_{3-10}$ alkyl or $C_{2-10}$ alkenyl group which may be substituted by a $C_{4-6}$ cycloalkyl group, a $C_{6-10}$ aryl or $C_{4-10}$ heteroaryl group, a $C_{4-6}$ cycloalkyl group which may be substituted by a $C_{1-6}$ alkyl group, a $C_{6-10}$ aryl or $C_{4-10}$ heteroaryl group or a $C_{6-10}$ aryl group. Even more preferably, $R_{21}$ represents a hydrogen atom, a linear $C_{1-10}$ or branched $C_{3-10}$ alkyl group or linear $C_{2-10}$ or branched $C_{3-10}$ alkenyl group which may be substituted by a cyclohexyl group or a phenyl group, or a cyclohexyl group which may be substituted by a $C_{1-4}$ alkyl group. Yet even more preferably, $R_{21}$ represents an unsubstituted $C_{1-10}$ alkyl group or $C_{2-10}$ alkenyl group, still even more preferably an unsubstituted $C_{2-6}$ alkyl group or $C_{3-6}$ alkenyl group, and most preferably an ethyl group or an allyl group.

The (meth)acrylate compounds of formulae (A), (B) and (C) may be selected from the group consisting of methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylate ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy]ethyl ester (CAS no. 72869-86-4)_(UDMA), glycerol mono- and di-acrylate such as 1,3-glycerol dimethacrylate (GDM), glycerol mono- and dimethacrylate, ethylene glycol diacrylate, ethylene glycol dimethacrylate, polyethylene glycol diacrylate (where the number of repeating ethylene oxide units vary from 2 to 30), polyethylene glycol dimethacrylate (where the number of repeating ethylene oxide units vary from 2 to 30 especially triethylene glycol dimethacrylate ("TEGDMA"), neopentyl glycol diacrylate, neopentyl glycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxyethyl hexamethylene dicarbamate, di-2-methacryloyloxyethyl trimethylhexanethylene dicarbamate, di-2-methacryloyloxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethyl-hexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)] propane, 2,2'-bis[4(2-hydroxy-3-acryloxy-phenyl)propane, 2,2'-bis(4-methacryloxyethoxyphenyl)propane, 2,2'-bis(4-acryloxyethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl) propane, 2,2'-bis(4-acryloxydiethoxyphenyl)propane, 2,2'-bis[3(4-phenoxy)-2-hydroxypropane-1-methacrylate] propane, and 2,2'-bis[3(4-phenoxy)-2-hydroxypropane-1-acrylate]propane.

Most preferably, a compound of formula (B) selected from the group consisting of:

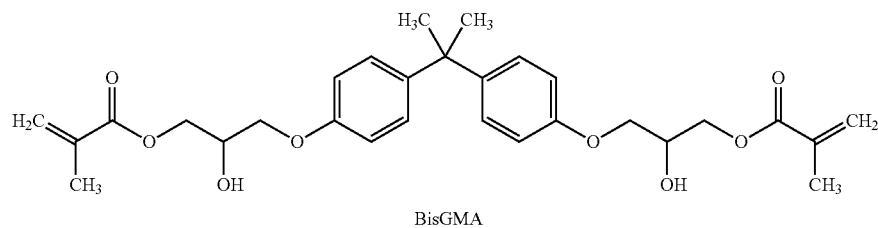

BisGMA

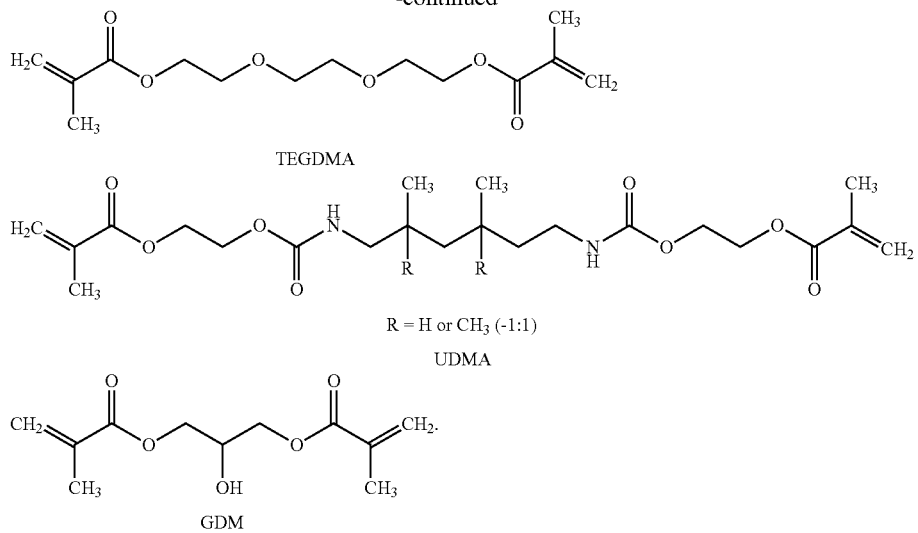

Particular preferred mono- or bis- or (me)acrylamides and poly[(meth) acrylamides] have the following formulae (D), (E) and (F):

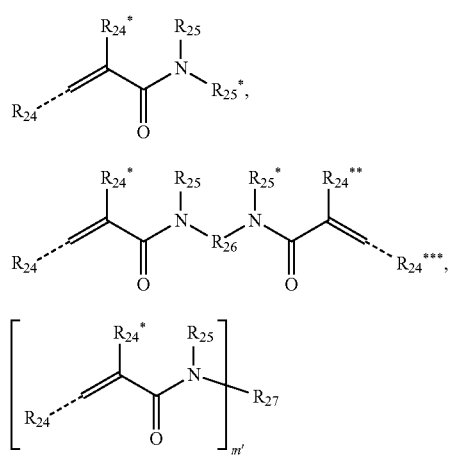

wherein $R_{24}$ $R^*_{24}$, $R^{}_{24}$, $R^{*}_{24}$ have the same meaning as $R_{20}$ $R^*_{20}$, $R^{}_{20}$, $R^{*}_{20}$ defined above for formulae (A), (B) and (C). $R_{25}$, $R^*_{25}$ independently represent a residue having the same meaning as $R_{21}$ defined above for formula (A), and $R_{27}$ and m' have the same meaning as $R_{23}$ and m defined above for formula (C).

In formula (E), $R_{26}$ represents a divalent substituted or unsubstituted organic residue having from 1 to 45 carbon atoms, whereby said organic residue may contain at least one of 1 to 7 $C_{3-12}$ cycloalkylene group(s), 1 to 7 $C_{6-14}$ arylene groups, from 1 to 7 carbonyl groups, 1 to 7 carboxyl groups (—(C=O)—O— or —O—(C=O)—), 1 to 7 amide groups (—(C=O)—NH— or —NH—(C=O)—), 1 to 7 urethane groups (—NH—(C=O)—O— or —O—(C=O)—NH—), and 1 to 14 heteroatoms selected from oxygen, nitrogen and sulphur, which divalent organic residue may be substituted with one or more substituent(s) selected from the group consisting of a hydroxyl group, a thiol group, a $C_{6-14}$ aryl group, —COOM, —PO$_3$M, —O—PO$_3$M$_2$ or —SO$_3$M*. Preferably, $R_{26}$ is a $C_1$ to $C_{18}$ alkylene group or a $C_2$ to $C_{18}$ alkenylene group which may contain at least one of 1 to 4 $C_{6-10}$ arylene groups and $C_{3-8}$ cycloalkylene group, 1 to 4 urethane groups (—NH—(C=O)—O— or —O—(C=O)—NH—), and 1 to 8 oxygen atoms or nitrogen atoms.

For $R_{25}$, the phrase "divalent organic residue may contain at least one of . . . " has an analogous meaning as defined above for $R_{22}$ of compound of formula (B).

In formulae (D), (E), (F), the dotted bond indicates that $R_{24}$ and $R^{***}_{24}$ may be in (Z) or (E) configuration relative to CO.

In compound of formula (D), $R_{25}$ and $R_{25*}$ may cooperatively form a ring in which $R_{25}$ and $R_{25*}$ are linked by a C—C bond or a functional group selected from the group consisting of an ether group, a thioether group, an amine group and an amide group.

Preferred methacrylamides according to formulae (D), (E), (F) have the following formulae:

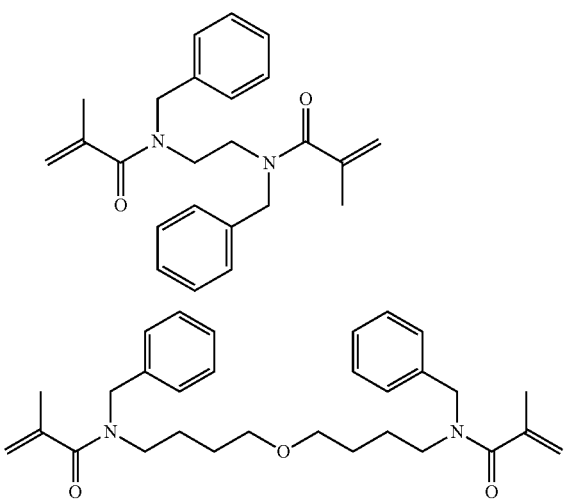

31
-continued
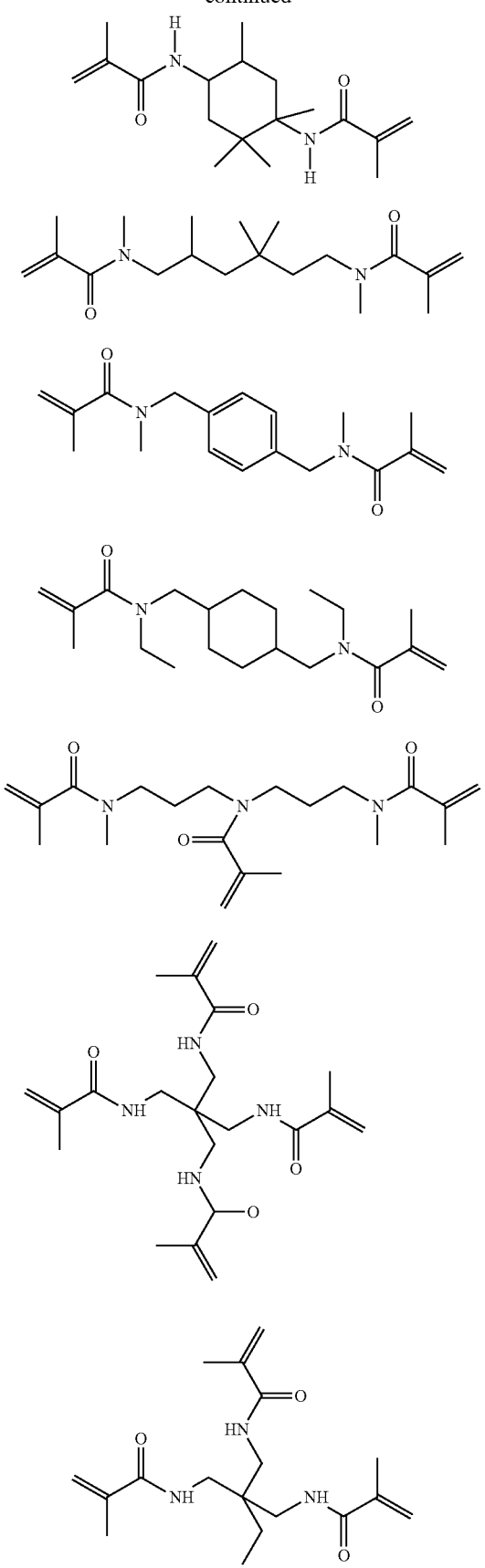
32
-continued
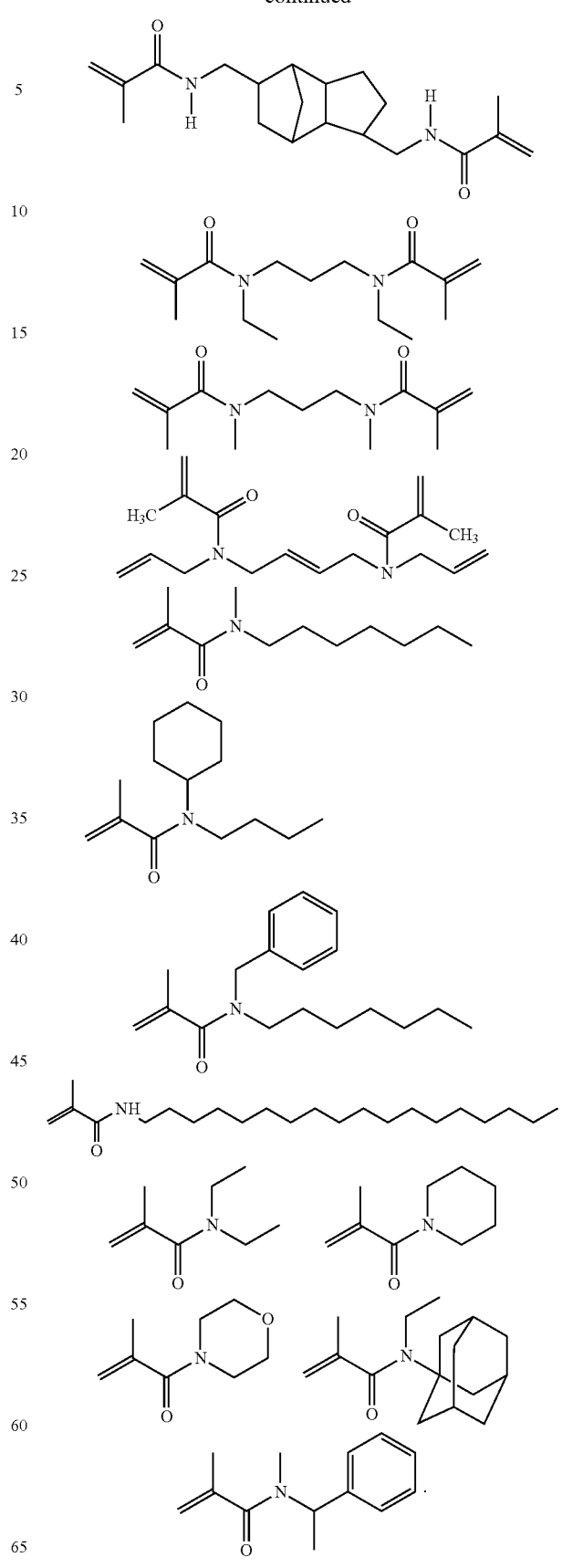

Preferred acrylamides according to formulae (D), (E), (F) have the following formulae:
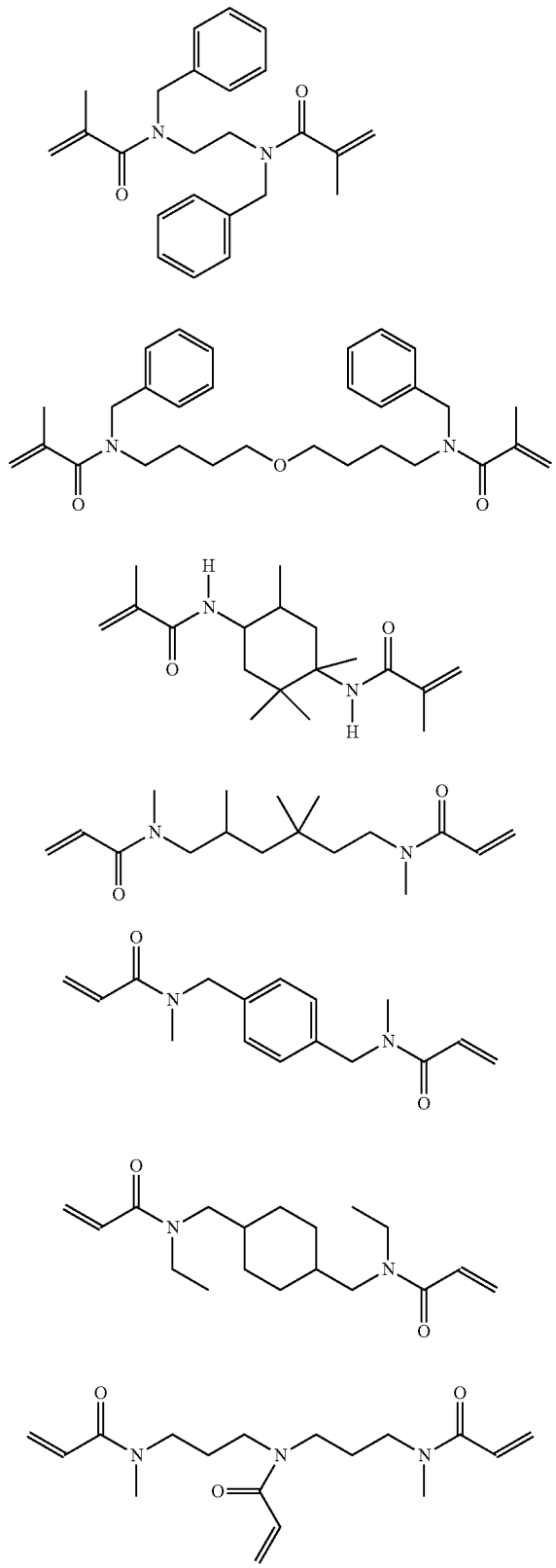
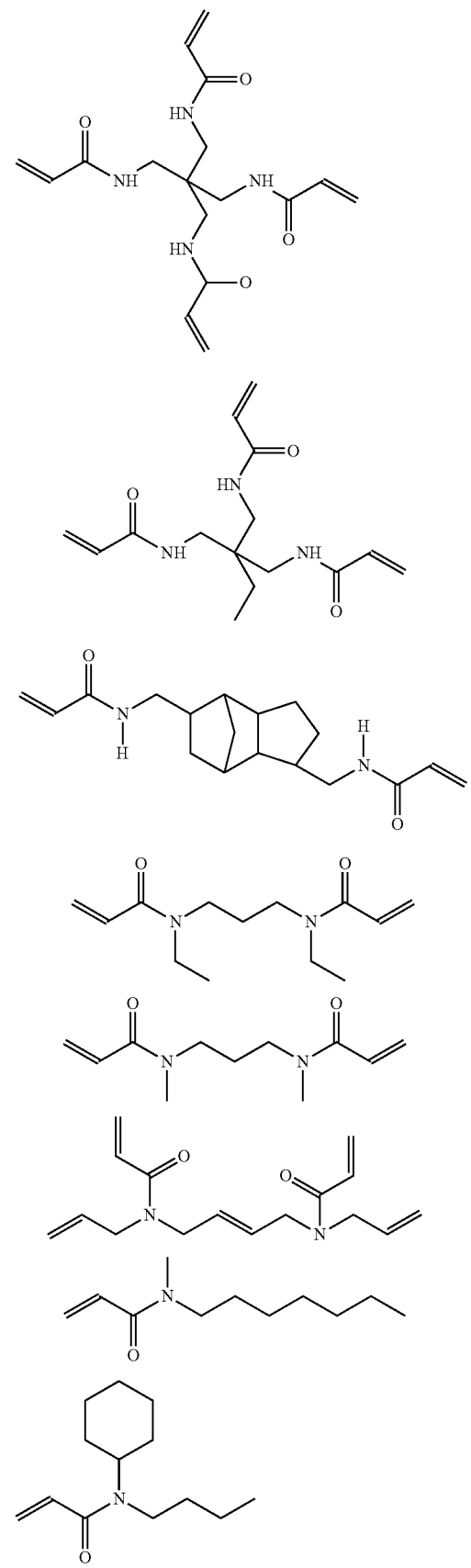

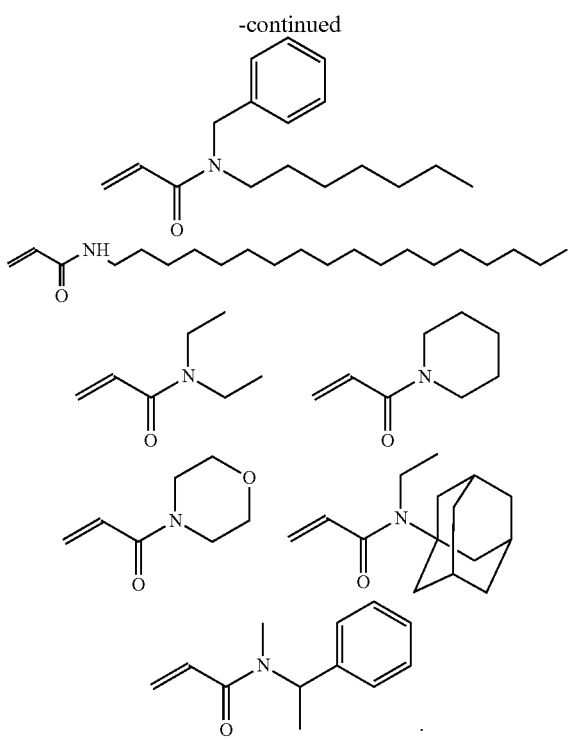

Most preferred are the following bisacrylamides:

N,N'-diallyl-1,4-bisacrylamido-(2E)-but-2-en (BAABE) having the structural formula

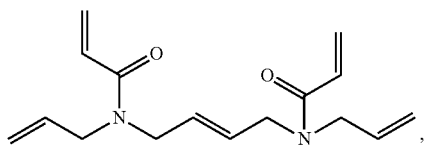 [SMILES: C=CCN(C/C=C/CN(CC=C)C(=O)C=C)C(=O)C=C]

and
N,N'-diethyl-1,3-bisacrylamido-propan (BADEP) having the structural formula

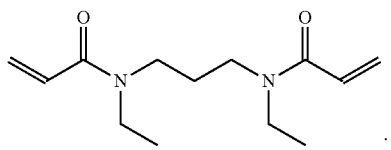 [SMILES: C=CC(=O)N(CC)CCCN(CC)C(=O)C=C]

Particularly preferred further polymerizable compound(s) (c) are selected from N-substituted alkylacrylic or acrylic acid amide monomers, preferably from compounds of formulae (A), (B), (D) and (E), more preferably from compounds of formulae (D) and (E), and most preferably from compounds of formula (E).

Further polymerizable compound(s) (c) in the form of polymers are preferably selected from polymerizable polyacidic polymers.

The term "polymerizable" as used with the term "polymerizable polyacidic polymer" means a polymer capable of combining by covalent bonding in an addition polymerization. The "polymerizable polyacidic polymer" may be covalently combined by means of polymerization with a cross-linker as well as e.g. with a monomer having a polymerizable (carbon-carbon) double bond, to form graft polymers and/or crosslinked polymers when curing the dental composition.

The term "polyacidic" as used with the term "polymerizable polyacidic polymer" means that the polymer has a plurality of acidic groups, preferably carboxylic acid groups, which may participate in a cement reaction with a reactive glass. The carboxylic acid groups are preferably present in the backbone and derived from acrylic acid, methacrylic acid and/or itaconic acid.

Further Optional Components

The dental composition according to the present invention may comprise additional optional components besides of the above described components.

For example, the dental composition according to the present invention may comprise suitable solvent(s).

Preferably, the solvent(s) are selected from (d) organic water soluble solvent(s) and/or water. Organic water soluble solvent(s) may be selected from the group consisting of alcohols such as ethanol, propanol (n-, i-), butanol (n-, iso-, tert.-), ketones such as acetone, methyl ethyl ketone (MEK), diisopropyl ketone, and polar aprotic solvents such as DMSO.

For a dental composition in the form of a dental infiltrant, DMSO is particularly preferred as organic water soluble solvent.

The dental composition of the present invention may comprise the solvent(s) in an amount of 5 to 75 percent by weight based on the total weight of the composition.

Preferably, the dental composition according to the present invention is free of water.

The dental composition according to the present invention may comprise (e) a filler. The dental composition may comprise one or more filler(s) (e). Preferably, the filler(s) (e) are selected from particulate glass fillers, silanated glass flakes, granulated prepolymerized fillers, ground prepolymerized fillers and filler aggregates.

The term "particulate glass filler" refers to a solid mixture of mainly metal oxides transformed by a thermal melt process into a glass and crushed by various processes. The glass is in particulate form. Moreover, the particulate glass filler may be surface modified, e.g. by silanation or acid treatment.

For the filler (e), a glass component may be selected from "inert glass(es)", "reactive glass(es)" and "fluoride releasing glass(es)".

The term "inert glass(es)" refers to a glass which is not capable of reacting with a polymer containing acidic groups in a cement reaction. Inert glasses are for example described in the Journal of Dental Research June 1979, pages 1607-1619, or more recently in U.S. Pat. Nos. 4,814,362, 5,318, 929, 5,360,770, and application US 2004/0079258 A1. Specifically, from US 2004/0079258 A1, inert glasses are known in which strongly basic oxides such as CaO, BaO, SrO, MgO, ZnO, $Na_2O$, $K_2O$, $Li_2O$ etc. are replaced with weakly basic oxides such as those in the Scandium or Lanthanide series.

The term "reactive glass(es)" refers to a glass which is capable of reacting with a polymer containing acidic groups in a cement reaction. The glass is in particulate form. Any conventional reactive dental glass may be used for the purpose of the present invention. Specific examples of particulate reactive glasses are selected from calcium alumino silicate glass, calcium alumino fluorosilicate glass, calcium aluminumfluoroborosilicate glass, strontium aluminosilicate glass, strontium aluminofluorosilicate glass, strontium aluminofluoroborosilicate glass. Suitable reactive glasses may be in the form of metal oxides such as zinc oxide and/or magnesium oxide, and/or in the form of ion-leachable glasses, e.g., as described in U.S. Pat. Nos. 3,655,605, 3,814,717, 4,143,018, 4,209,434, 4,360,605 and 4,376,835.

The term "fluoride releasing glass(es)" refers to a glass capable to of releasing fluoride. Fluoride releasing capability may be provided by adding to a mixture of oxides for forming a glass inorganic particles containing fluoride with the proviso that the glass has fluoride releasability, preferably sustained fluoride releasability. Such inorganic particles may be selected from the group consisting of sodium fluoride, strontium fluoride, lanthanum fluoride, ytterbium fluoride, yttrium fluoride, and calcium-containing fluoroaluminosilicate glasses.

Preferably, the particulate glass filler is a reactive glass or a fluoride releasing glass as defined above, more preferably a reactive glass.

Most preferably, the particulate glass filler is a reactive particulate glass filler comprising:
1) 20 to 45% by weight of silica,
2) 20 to 40% by weight of alumina,
3) 20 to 40% by weight of strontium oxide,
4) 1 to 10% by weight of $P_2O_5$, and
5) 3 to 25% by weight of fluoride.

The present dental composition preferably comprises 20 to 90 percent by weight of the particulate glass filler, more preferably 30 to 80 percent by weight, based on the total weight of the composition.

The particulate glass filler usually has an average particle size of from 0.005 to 100 μm, preferably of from 0.01 to 40 μm, more preferably of from 0.05 to 20 μm, most preferably of from 0.1 to 3 μm as measured, for example, by electron microscopy or by using a conventional laser diffraction particle sizing method as embodied by a MALVERN Mastersizer S or MALVERN Mastersizer 3000 apparatus.

The particulate glass filler may have a unimodal or multimodal (e.g., bimodal) particle size distribution, wherein a multimodal particulate glass filler represents a mixture of two or more particulate fractions having different average particle sizes.

The term "silanated" as used herein means that the filler has silane coupling agent(s) on its surface, for example in the form of a coating at least partly, and preferably fully covering the surface of the filler.

Typically, the silane coupling agent(s) are organosilanes of formula (Y)

$$(R_{14},R_{15},R_{16})Si(R_H)_n \qquad (Y)$$

are applied, wherein n is 1 to 3 and the number of substituents $R_{14}$, $R_{15}$, $R_{16}$ is 4-n, wherein at least one of $R_{14}$, $R_{15}$, $R_{16}$ represents a polymerizable group. $R_H$, which may be the same or different if two or three groups $R_H$ are present, represent(s) a hydrolysable group capable of reacting with the surface of the filler material to be coated. $R_H$ may be selected from the group consisting of alkoxy groups, ester groups, halogen atoms and amino group, wherein the alkoxy groups are preferably linear $C_{1-8}$ or branched or cyclic $C_{3-8}$ alkoxy groups, and the ester groups are preferably carboxylates having linear $C_{1-8}$ or branched or cyclic $C_{3-8}$ alkyl groups. Most preferably, the hydrolysable group $R_H$ represents an alkoxy group.

The groups $R_{14}$, $R_{15}$ and $R_{16}$ may be the same or different and represent unreactive groups and/or polymerizable groups, with the proviso that at least one of $R_{14}$, $R_{15}$ and $R_{16}$ represents a polymerizable group. Unreactive groups for $R_{14}$, $R_{15}$ and $R_{16}$ may be represented by alkyl groups, preferably linear $C_{1-8}$ or branched or cyclic $C_{3-8}$ alkyl groups. Polymerizable groups for $R_{14}$, $R_{15}$ and $R_{16}$ are preferably selected from the group consisting of a (meth) acryl group, a vinyl group or an oxirane group, more preferably (meth)acryl group or a vinyl group, and most preferably a (meth)acryl group which may be in the form of e.g. methacryloxy or methacryloxyalkyl wherein alkyl means a linear $C_{1-8}$ or branched or cyclic $C_{3-8}$ alkyl group.

Particularly preferred organosilanes are for example 3-methacryloxy trimethoxysilane, vinyltrichlorosilane, tris (2-methoxyethoxy)-vinylsilane or tris(acetoxy)-vinylsilane, or any one of the specific group of organosilanes disclosed in EP 0 969 789 A1, namely 3-methacryl-oxypropyltrimethoxysilane, 3-methacryloxypropyldimethoxy-monochlorosilane, 3-methacryl-oxypropyldichloromonomethoxysilane, methacryloxypropyltri-chlorosilane, 3-methacryloxy-propyldichloromonomethyl-silane and 3-methacryloxypropylmonochlorodimethylsilane.

Alternatively or additionally to the organosilanes of formula (Y), so-called dipodal organosilanes may be applied. Dipodal organosilanes are typically compounds of formula (Z)

$$((R_{14},R_{15},R_{16})Si-R_7)_2CH-R_H \qquad (Z),$$

wherein $R_{14}$, $R_{15}$, $R_{16}$ and $R_H$ have the same meaning as defined above for the organosilane of formula (Y), and $R_{17}$ represents an alkylene group, preferably a linear $C_{1-8}$ or branched or cyclic $C_{3-8}$ alkylene group.

The term "flake" as used herein means that the glass is in the form of a flake, that is its long diameter is larger than its thickness, at least by factor 2. The ratio of average long diameter to average thickness is termed "average aspect ratio" herein.

The aforementioned filler aggregates may be obtained by a process comprising:

a) coating a particulate filler, preferably a particulate glass filler as described above, which has a median particle size (D50) of from 1 to 1200 nm, with a coating composition containing a polymerizable film-forming agent forming a polymer coating layer on the surface of the particulate filler, said polymer coating layer may display reactive groups on the surface of the coating layer, said reactive groups being selected from addition polymerizable groups and step-growth polymerizable groups, thereby forming a coated particulate filler; subsequently or concurrently b) agglomerating the coated particulate filler, optionally in the presence of a further crosslinking agent and optionally in the presence of a further particulate filler not displaying reactive groups, for providing a granulation of the coated particulate filler wherein the granulation contains the coated particulate filler particles and the optional further particulate filler particles separated from and connected to each other by at least one coating layer, whereby the at least one coating layer may be crosslinked by crosslinking groups obtained by reacting the reactive groups and optionally a further crosslinking agent;

c) optionally milling, classifying and/or sieving the granulation of the coated particulate filler; and d) optionally further crosslinking the granulation of the coated particulate filler; for providing composite filler particles having a median particle size (D50) of from 1 to 70 μm, wherein reactive groups are transformed into crosslinking groups obtained by reacting reactive groups and optionally a further crosslinking agent, and wherein the particulate filler is the main component by volume of the composite filler particles as further described in EP 2 604 247 A1.

For obtaining granulated and ground prepolymerized fillers, step b) of the above described process is omitted, and the milling step c) is applied with a suitable milling apparatus to attain an appropriate granulation particle size or ground particle size.

The dental composition according to the present invention preferably contains the filler (e) in an amount of 1 to 85 percent by weight based on the total weight of the composition.

A particularly preferred filler (e) contains:
(e-1) one or more particulate glass filler(s) having an average particle size of from 0.1 to 3 µm; and
(e-2) one or more silanated glass flake(s),
  (i) wherein the silanated glass flakes have an average thickness between 50 nm and 1000 nm; and
  (ii) wherein the silanated glass flakes have an average aspect ratio (long diameter/thickness) in the range of from 2:1 to 50:1.

The "average thickness" as used herein may be determined as follows: The thicknesses of 100 or more glass flakes of a sample are determined by scanning electron microscopy (SEM). Then, the total of the measured thicknesses is divided by the number of glass flakes for which the thickness was determined.

In the particularly preferred filler (e), the particulate glass filler (e-1) has an average particle size of from 0.1 to 3 µm, preferably 0.2 to 2 µm, more preferably from 0.3 to 1.5 µm, most preferably from 0.5 to 1.2 µm. When the average particle size of the particulate glass filler (e-1) is less than 0.1 µm, then the handling properties of the dental composition may deteriorate. When the average particle size of the particulate glass filler (e-1) is more than 3.0 µm, then the gloss properties of the cured dental composition may deteriorate.

Preferably, the particulate glass filler (e-1) is a reactive glass or a fluoride releasing glass. More preferably, the particulate glass filler (e-1) is a reactive glass.

Preferably, the dental composition contains the particulate glass filler (e-1) in an amount of 0.5 to 60 percent by weight, preferably 1 to 50 percent by weight, more preferably 3 to 40 percent by weight based on the total weight of the composition.

The particulate glass filler (e-1) preferably has a sphericity of at least 0.5, more preferably at least 0.9, and most preferably at least 0.95.

The term "sphericity" as used herein means the ratio of the surface area of a sphere with the same volume as the given particle in the form of the particulate glass filler (e-1) to the surface area of the particle in the form of the particulate glass filler (e-1).

Preferably, the particulate glass filler (e-1) is silanated, more preferably silanated with an organosilane as defined above.

The silanated glass flakes (e-2) preferably have an average thickness between 50 nm and 1000 nm, and/or an average aspect ratio (long diameter/thickness) in the range of from 2:1 to 50:1. While the above described average thickness of the silanated glass flakes is from 50 to 1000 µm, the amount by weight of fractions of silanated glass flakes having different thickness may vary in a sample, wherein preferably, the silanated glass flakes include a fraction of silanated glass flakes having a thickness of 30 nm to 1500 nm, more preferably a thickness of 40 nm to 1000 nm, in an amount of at least 90% by weight.

Owing to the specific selection of average thickness and average aspect ratio of the silanized glass flakes (e-2), excellent gloss and gloss retention can be obtained and ensured for a long period of time. According to the present invention, self-alignment of the silanized glass flakes (e-2) within the polymer matrix of the cured dental composition is possible, whereby the glass flakes may arrange by partially overlapping. Planar and overlapping self-alignment provides a smooth surface of the cured dental composition. Therefore, the dental composition will have an improved initial gloss compared to conventional composition containing glass in the form of spheres or fibers.

The term "gloss" as used herein means the optical property indicating how good or bad a surface reflects light in a specular direction. Gloss is affected by the refractive index of the material, the angle of incident light and the surface topography. Apparent gloss depends on the amount of specular reflection, that is light reflected from the surface in an equal amount and the symmetrical angle to the one of incoming light. The specular reflection can be calculated by the Fresnel equation, which is well known in the field of optics. Surface roughness in micrometer range influences the specular reflection levels. A low intensity of specularly reflected light means the surface is rough and it scatters the light in other directions. Specifically, a totally nonreflective surface has zero gloss units (G.U.), while a perfect mirror would have 1000 G.U. at a measuring angle of 60°. Typically, for gloss measurement, a measuring angle of 60° is applied, since this angle is considered to be the best angle to use so as to provide the closest correlation to a visual observation. 10 G.U. or less means low gloss, 10 to 70 G.U. are considered as semigloss, and a gloss >70 G.U. is considered as high gloss. For dental restorations prepared from the cured dental composition according to the present invention, semigloss (10 to 70 G.U.) and high gloss (>70 G.U.) are preferred, wherein high gloss is particularly preferred.

The specific selection of the silanized glass flakes (e-2) provides not only improved initial gloss, but also renders possible gloss retention for a relatively long period of time.

The term "gloss retention" as used herein means that the cured dental composition retains its initial gloss for a relatively long period of time, even when exposed to processing by a material removal method such as sanding or polishing, or likewise when the cured dental composition is exposed to typical daily loads such as tooth brushing, saliva fluid in the oral cavity and teeth grinding or clenching by the patient. It is readily understood that the planar, overlapping alignment of the glass flakes is more stable to the aforementioned loads, because in this arrangement, it is less likely that glass flake particles are removed by a mechanical load. That is, the surface of the cured dental composition will stay smooth for a relatively long time. Furthermore, regarding chemical resistance, for example in view of saliva fluid and/or acids from food, the planar, overlapping alignment of the glass flakes forms a kind of barrier which protects the cured dental composition as well as the tooth behind it from degradation by chemical influences such as acidity.

In addition, the silanated glass flakes (e-2) may provide for an advantageous viscosity of the uncured dental composition. In particular, the silanated glass flakes (e-2) may provide for a thixotropic behaviour of the dental composition.

According to the present invention, the combination of the particulate glass filler(s) (e-1) and silanated glass flakes (e-2) is suitable for adjusting the viscosity of the dental composition within a desired range. The silanated glass flakes (e-2) may also be advantageous in terms of the mechanical properties and long-term mechanical resistance of the cured dental composition owing to the advantageous arrangement in the form of planar, overlapping alignment of the glass flakes, which arrangement may provide for uniform reinforcement and increased dimensional stability.

The combination of the silanated glass flakes (e-2) and the particulate glass filler(s) (e-1) is specifically selected in order to attain well balanced properties for the cured dental composition. Owing to the specific combination of silanated glass flakes (e-2) and the particulate glass filler(s) (e-1), excellent gloss, gloss retention and long-term chemical resistance may be attained as well as excellent mechanical properties and long-term mechanical resistance. The small, nano-sized silanated glass flakes (e-2) readily arrange between and around the particulate glass filler(s) (e-1) which may be considerable larger with up to 3 μm. Thereby, the small, nano-sized silanated glass flakes (e-2) may self-align in the form of the above described planar, overlapping alignment, which may provide for a kind of barrier or shield effect. That is, the large particulate glass filler(s) (e-1) particles are prevented from being removed from the cured dental composition by mechanical forces or chemical influences, since they are shielded by the planar, overlapping alignment of the silanated glass flakes (e-2). As a result of this shielding, instead of a large particulate glass filler(s) (e-1), at best, if that, the small, nano-sized silanated glass flakes (e-2) are removed from the cured dental composition. Owing to this shield effect, an excellent gloss retention is attained, since after removal of a small particle, the surface of the cured dental composition will still be smooth and have an excellent gloss compared to a cured composition from which a large particle is removed, which results in a significantly irregular surface having a significantly deteriorated gloss. Furthermore, it is feasible that the above described shielding effect also provides for both a good mechanical and chemical resistance, since the shielding effects prevents aggressive chemical influences, such as acidic fluids, to infiltrate the large particle, which infiltration may result in removal of the particle when a mechanical force is applied, whereby gloss and long-term mechanical resistance is deteriorated.

It is easily understood that when the particulate glass filler(s) (e-1) would be smaller than the glass flakes (e-2), as taught for example in US 2006/0241205 A1, it is unlikely that the above described shielding effect is attained. Because, glass flakes being larger than the a structural filler in the form of e.g. a (spherical) glass filler particles may not readily arrange between and around the (spherical) glass filler particles, but rather, separate layers of (spherical) glass filler particles and glass flakes may form, since the large glass flakes may not be able to arrange in a planar, overlapping alignment between the small (spherical) glass filler particles. However, in case a layer of large glass flakes covers the (spherical) glass filler particles, the large glass flakes may be easily removed from the surface of the cured dental composition by mechanical forces or chemical influences. Then, the deterioration of gloss as well as chemical and mechanical resistance will be significantly higher compared to the dental composition according to the invention.

Preferably, the particulate glass filler(s) (e-1) has/have an average particle size of from 0.3 to 2, more preferably of from 0.4 to 1.2.

For silanated glass flakes (e-2), it is preferred that they have an average thickness between 80 nm and 1000 nm.

Most preferably, the particulate glass filler(s) (e-1) has/have an average particle size of from 0.4 to 1.2, and the silanated glass flakes (e-2) have (a) an average thickness between 50 nm and 1000 nm, and (b) an average aspect ratio (long diameter/thickness) in the range of from 2:1 to 50:1.

The glass of the silanated glass flakes (e-2) preferably comprises the following components as oxides in percent by weight:
$SiO_2$=64-70
$B_2O_3$=2-5
$ZnO$=1-5
$Na_2O$=8-13
$MgO$=1-4
$CaO$=3-7
$Al_2O_3$=3-6,
and up to 3 percent of $K_2O$ and $TiO_2$.

The glass of the silanated glass flakes (e-2) is preferably an inert glass, wherein the term "inert glass" has the same meaning as described above for the particulate glass filler(s) (e-1).

The silanated glass flakes (e-2) are preferably obtainable by milling glass flakes having an aspect ratio of at least 20:1, and subsequently silanating the milled glass flakes. The milling of the glass flakes is not particularly limited and may be carried out with any apparatus typically applied for milling filler materials, such as a ball milling apparatus.

The thus obtained milled glass flakes may be silanated with a silane having one or more polymerizable groups reactive with the polymerizable compounds (ii). Silanes for silanating filler materials of dental compositions are well known and a large variety thereof for dental applications is described for example by J. M. Antonucci, Journal of Research of the National Institute of Standards and Technology, 2005, vol. 110, no. 5, pages 541 to 558.

The silanated glass flakes (e-2) preferably have a particle size distribution determined by light scattering, wherein at least 70 percent, more preferably at least 75 percent, even more preferably at least 80 percent of the particles have a particle size of less than 50 μm.

It is preferred that the silanated glass flakes (e-2) have a refractive index in the range of 1.46 to 1.60.

The particulate glass filler(s) (e-1) and the silanated glass flakes (e-2) may be suitably selected, preferably by selecting a ratio of the average particle size of the particulate glass filler(s) (e-1) and the average thickness of the silanated glass flakes (e-2) within the range of 10:1 to 1:1, more preferably 7:1 to 1.2:1, most preferably 4:1 to 1.4:1.

Preferably, the dental composition contains the silanated glass flakes (e-2) in an amount of from 0.5 to 40 percent, more preferably 1 to 30 percent, even more preferably 3 to 20 percent by weight based on the total weight of the composition.

In the dental composition, the ratio of the weight of particulate glass filler(s) (e-1) and the weight of the silanated glass flakes (e-2) is preferably in the range of from 80:1 to 0.5:1, more preferably 40:1 to 1:1, even more preferably 20:1 to 1.5:1, yet even more preferably 10:1 to 2:1 and most preferably 5:1 to 2.5:1.

One-Part or Multi-Part Dental Composition

The dental composition according to the present invention may be a one-part or a multi-part dental composition.

The term "one-part" as used herein means that all components of the dental composition are comprised in one single part.

The term "multi-part" as used herein means that the components of the dental composition are comprised in a multitude of separate parts. For example, a first part of components is comprised in a first part, while as second part of components is comprised in a second part, a third part of components may be comprised in a third part, a fourth part of components may be comprised in a fourth part, and so on.

Preferably, the dental composition is a one-part or a two-part dental composition, more preferably a one-part dental composition.

For the one-part dental composition, it is preferred that it is free of water, and optionally also free of organic solvent(s). Because, water and/or organic solvent(s) may provide for an undesired activation of the polymerization initiator system, in particular of a redox initiator system, during storage of the dental composition.

For the two-part dental composition, it is preferred that the first part comprises at least the polymerization initiator system (b), which is preferably in solid form, and optionally solid components such as filler(s) (e), e.g. particulate glass filler. The second part preferably comprises at least the polymerizable compound (a), and optionally organic water soluble solvent(s) and/or water. It is preferred that the second part is free of water.

Characteristics of the Dental Composition

Preferably, the dental composition according to the invention is acidic. More preferably, it has a pH of at most 6, and most preferably a pH of at most 4.

The aforementioned pH value of the aqueous dental composition may be suitably adjusted depending on the components comprised in the dental composition as well as on the intended application. The pH of the dental composition may be adjusted by any means known in the art, e.g. by adding predetermined amounts of one or more acidic compounds to the aqueous dental composition. In this context, the term "acidic compounds" denotes compounds having a $pK_a$ within the range of about −10 to 50. Examples of suitable inorganic acids are sulfuric acid, phosphonic acid, phosphoric acid, hydrochloric acid, nitric acid and the like, which may be used alone or in combination with each other. Examples of suitable organic acids are carboxylic acids which are preferably selected from the group consisting of formic acid, acetic acid, lactic acid, citric acid, itaconic acid, poly(meth)acrylic acid, itaconic acid, maleic acid, polyvinyl phosphonic acid, polyvinyl phosphoric acid, trifluoromethane sulfonic acid, toluene sulfonic acid, methane sulfonic acid, succinic acid, malic acid, tannic acid, toluene sulfonic acid, adipic acid, tartaric acid and ascorbic acid. The set pH-value of the aqueous dental composition may be stabilized by means of a typical chemical buffer system, that is a combination of a weak organic or inorganic acid having a $pK_a$ value at a temperature of 20° C. within the range of about 9 to 50 and its corresponding salt. Alternatively, the buffer system may be in the form of a Norman Goods buffer (Good's buffer) representing organic compounds having a $pK_a$ value at a temperature of 20° C. in a range between about 6 and 8, having biochemical inertness and being suitable for application in a biological system such as the human body. Examples for typical chemical buffer systems are acidic acid/acetate buffer, dihydrogenphosphate/monohydrogenphosphate buffer or a citric acid/citrate buffer. Examples for Good's buffers are 4-(2-hydroxyethyl)-1-piperazineethanesulfonic acid (HEPES), 2-(N-morpholino)ethanesulfonic acid (MES) or N-cyclohexyl-3-aminopropanesulfonic acid (CAPS). In connection with the term "pH-value" it is noted that the pH-value/system typically relates to aqueous systems wherein water is the main compound, which may for example be present in an amount of about 55 to 90 percent by weight of the liquid phase of the dental composition. The pH-value of the dental composition may be determined by suitable standard means for determining the pH-value of aqueous systems, e.g. by means of a glass electrode.

For non-aqueous systems such as the present dental composition in the form of a preferred water-free formulation, the pH-value has to be determined for a system containing, instead of water, organic solvents. These organic solvents may e.g. be selected from the group consisting of alcohols such as ethanol, propanol (n-, i-), butanol (n-, iso-, tert.-), ketones such as acetone or the like. The determination of the pH-value of such non-aqueous systems containing these organic solvents may also be carried out by means of a glass electrode. However, for correctly determining the pH value, the instructions of the electrode's manufacturer for measuring pH values in non-aqueous systems have to be taken into account.

Polymerizable Compound of Formula (I') and Use Thereof

The present invention further relates to the polymerizable compound of the following formula (I'):

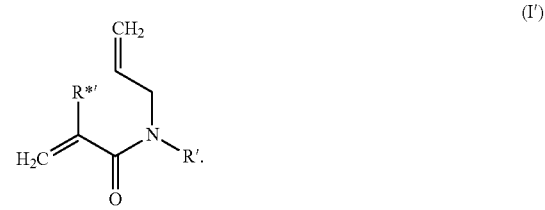

In formula (I'), R' represents a straight chain or branched $C_{5-18}$ alkyl or alkenyl group, which may be substituted by a group selected from a hydroxyl group, a $C_{1-4}$ alkoxy group, a tertiary amino group, and a carboxyl group. Optionally, in the main chain of the $C_{5-18}$ alkyl or alkenyl group, 1 to 8 carbon atoms may independently from each other be replaced by a heteroatom selected from an oxygen atom and a sulfur atom. R*' represents a hydrogen atom or a methyl group.

The term "tertiary amino group" in the definition of R' of formula (I') means an amino group substituted with two independently from each other selected $C_{1-4}$ alkyl groups, preferably methyl group(s).

Preferably, R' represents a straight chain $C_5$ or straight chain or branched $C_{6-18}$ alkyl or straight chain or branched $C_{5-18}$ alkenyl group, more preferably a straight chain or branched $C_{6-18}$ alkyl or alkenyl group, most preferably a straight chain or branched $C_{8-18}$ alkyl or alkenyl group, which may be substituted by a group selected from a hydroxyl group, a $C_{1-4}$ alkoxy group, a tertiary amino group, and a carboxyl group.

It is preferred that if in R' carbon atoms in the main chain are replaced by heteroatoms, in the main chain of an alkyl group of R', preferably of a linear alkyl group of R', 1, 2 or 5 to 8 carbon atoms, more preferably 5 to 8 carbon atoms, most preferably 6 to 8 carbon atoms may independently from each other be replaced by a heteroatom selected from an oxygen atom and a sulfur atom.

R*' represents a hydrogen atom or a methyl group.

Preferably, in the polymerizable compound of the following formula (I), R' is a group of the following formula (II'):

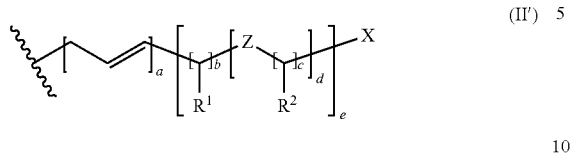

In formula (II'), X is a hydrogen atom, a hydroxyl group, a $C_{1-4}$ alkoxy group, a tertiary amino group or a carboxyl group, Z is an oxygen atom or a sulfur atom, and in case more than one Z is present, the Z may be the same or different. $R^1$ is a hydrogen atom or a group selected from a hydroxyl group, a $C_{1-4}$ alkyl group, a $C_{1-4}$ alkoxy group, a tertiary amino group, and a carboxyl group. In case more than one group $R^1$ is present, the groups may be the same or different. $R^2$ is a hydrogen atom or a group selected from a hydroxyl group, a $C_{1-4}$ alkyl group, a $C_{1-4}$ alkoxy group, a tertiary amino group, and a carboxyl group. In case more than one group $R^2$ is present, the groups may be the same or different.

In formula (II'), a is 0 or 1, b is an integer of from 2 to 18, c is an integer of from 2 to 16, d is an integer of from 0 to 8, and e is an integer of from 1 to 3, provided that when a=d=0, then b is at least 5, preferably at least 6, more preferably at least 7.

Preferably, in formula (II'), a is 0 or 1, b is an integer of from 5 to 18, c is an integer from 2 to 8, c is an integer from 0 to 8, and e is 1 or 2. More preferably, in formula (II'), a is 0 or 1, b is an integer of from 6 to 18, c is an integer from 2 to 4, d is an integer from 0 to 2 and 5 to 8, and e is 1 or 2. Most preferably, in formula (II'), a is 0 or 1, b is an integer of from 8 to 18, c is 2, d is 0 or an integer of from 5 to 8, and e is 1.

Preferably, the polymerizable compound of formula (I) is selected from the following structural formula of formulae (III') or (IV'):

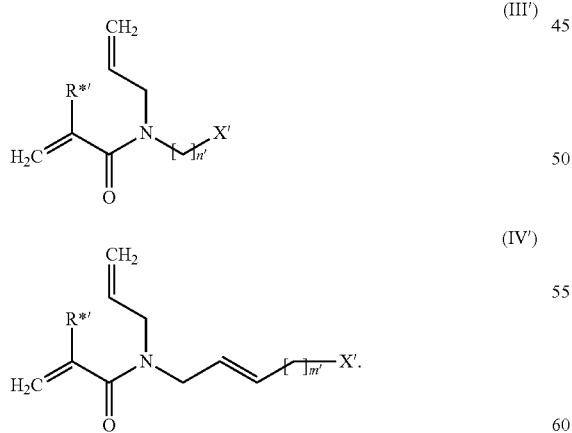

In formulae (III') and (IV'), R*' represents a hydrogen atom or a methyl group, preferably a hydrogen atom, X' is a hydrogen atom, a hydroxyl group, a tertiary amino group or a carboxyl group, n' is an integer of from 5 to 18, and m' is an integer of from 2 to 15.

Particular preferred compounds of formula (I') are selected from the following structural formulae:

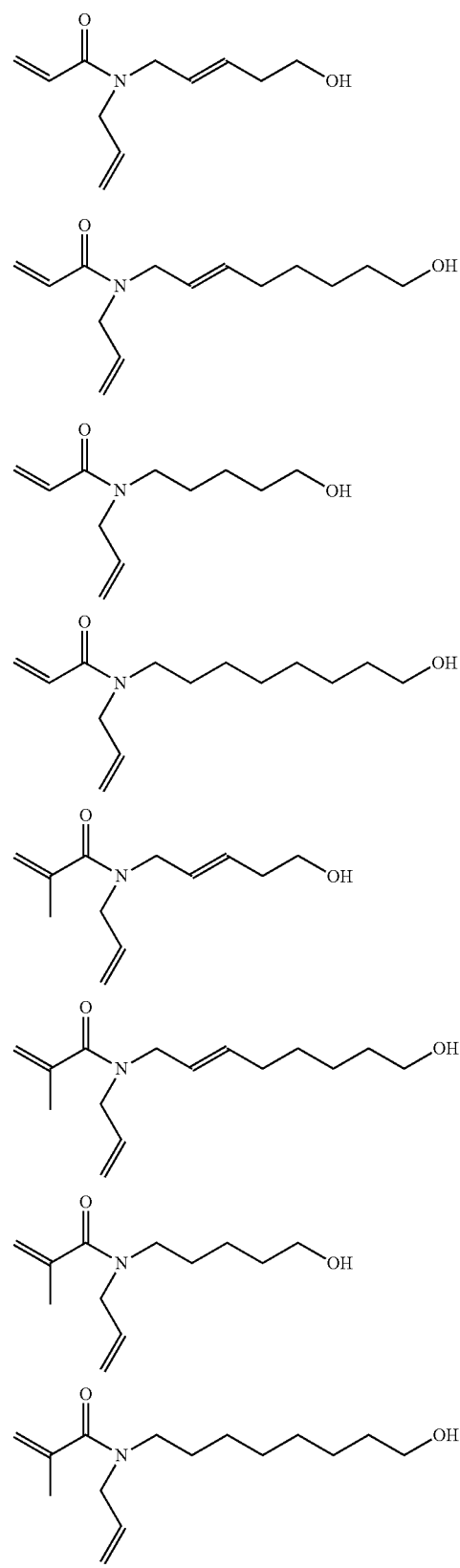

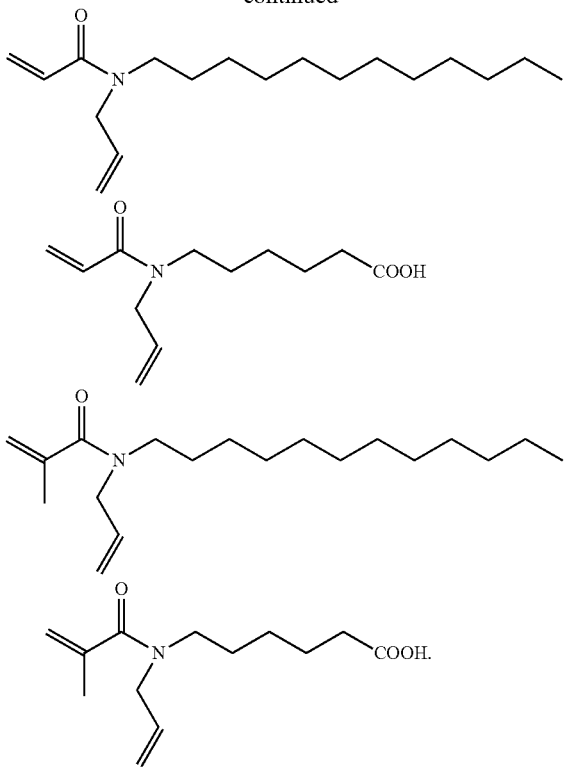

From the particularly preferred polymerizable compounds of formula (I') shown above, the acryloyl compounds are most preferred.

The polymerizable compound of formula (I') may be used in a dental composition, in particular in a dental composition as described above.

Particularly Preferred Embodiments

According to a particularly preferred embodiment, the dental composition according to the invention comprises (a) a polymerizable compound of the following formula (I*):

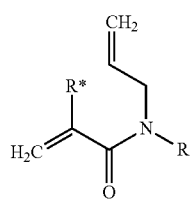
(I*)

wherein
R is a group of the following formula (II*)

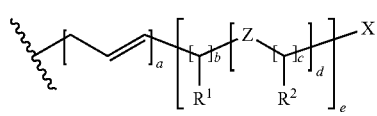
(II*)

wherein
X is a hydrogen atom, a hydroxyl group, a tertiary amino group or a carboxyl group;
Z is an oxygen atom;
R$^1$ is a hydrogen atom or a group selected from a hydroxyl group, a tertiary amino group, and a carboxyl group, and in case more than one group R' is present, the groups may be the same or different, preferably R$^1$ is a hydrogen atom;
R$^2$ is a hydrogen atom or a group selected from a hydroxyl group, a tertiary amino group, and a carboxyl group, and in case more than one group R$^2$ is present, the groups may be the same or different, preferably R$^2$ is a hydrogen atom;
a is 0 or 1,
b is an integer of from 2 to 18, preferably 2 to 12;
c is an integer of from 2 to 4, preferably b is 2;
d is an integer of from 0 to 8, preferably 0; and
e is an integer of from 1 to 3, preferably 1; and
R* represents a hydrogen atom or a methyl group; and
(b) a polymerization initiator system.

According to another particularly preferred embodiment, the polymerizable compound according to the present invention has the formula (I**):

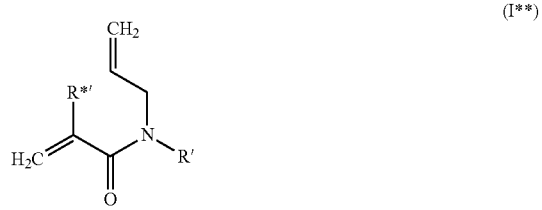
(I**)

wherein
R' is a group of the following formula (II**)

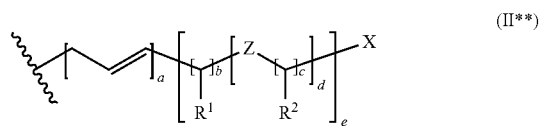
(II**)

wherein
X is a hydrogen atom, a hydroxyl group, a tertiary amino group or a carboxyl group;
Z is an oxygen atom;
R$^1$ is a hydrogen atom or a group selected from a hydroxyl group, a tertiary amino group, and a carboxyl group, and in case more than one group R' is present, the groups may be the same or different, preferably R$^1$ is a hydrogen atom;
R$^2$ is a hydrogen atom or a group selected from a hydroxyl group, a tertiary amino group, and a carboxyl group, and in case more than one group R$^2$ is present, the groups may be the same or different, preferably R$^{2'}$ is a hydrogen atom;
a is 0 or 1;
b is an integer of from 2 to 18, preferably 6 to 18;
c is an integer of from 2 to 4, preferably b is 2;
d is an integer of from 0 to 2 or 5 to 8, preferably 0; and
e is an integer of from 1 to 3, preferably 1,
provided that when a=d=0, then b is at least 5, preferably at least 6, more preferably at least 7; and
R* represents a hydrogen atom or a methyl group.

Furthermore, according to a particularly preferred embodiment, the polymerizable compound of formula (I**) is used in a dental composition.

The particularly preferred embodiments may be modified by any one of the features described above in the general part of the description.

The invention will now be further illustrated by the following Examples.

EXAMPLES

Preparation of N-Acryl-8-allylamino-octanol

A compound of formula (I) wherein R* represents a hydrogen atom and R represents octyl-8-ol was prepared starting from octane diol by a synthesis pathway comprising the following three steps:

Step 1: Preparation of 8-bromo-octanol 16 g (110 mmol) of octane diol have been dissolved in 250 ml toluene. After addition of 15.5 ml of HBr (137 mmol, 1.25 eq., 48% in water) the reaction mixture has been refluxed with a dean-stark receiver to remove the water from the reaction. After 8 hours the mixture was cooled to room temperature and was washed two times with distilled water and once with brine. After filtration over sodium sulfate and evaporation of the solvent the bromide was obtained in quantitative yield. In the NMR spectra, residual toluene was observed, which had no impact on the subsequent steps.

$D_{20°C}$=1.23 g/ml (lit: 1.22 g/ml)

$^{13}$C NMR (CDCl$_3$; ppm): 62.95 (CH$_2$OH), 34.04 (BrCH$_2$CH$_2$), 32.78/32.71 (BrCH$_2$) and (CH$_2$CH$_2$OH), 29.23/28.73/28.09/25.65 (CH$_2$)

Step 2: Preparation of 8-allylamino-octanol 18 g (130 mmol, 1.2 eq.) K$_2$CO$_3$ were suspended in 60 ml (800 mmol, 7.3 eq.) allylamine. 22.9 g 8-Bromo octanol dissolved in 20 ml dichloromethane was added dropwise over a period of 30 minutes. The mixture was stirred at room temperature overnight. After filtration and evaporation, the desired compound was obtained in 98% yield.

Step 3: Preparation of N-acryl-8-allylamino-octanol 15 g (81 mmol) 8-allylamino-octanol was dissolved in 100 ml THF, 5.54 g (136 mmol, 1.7 eq.) KOH dissolved in 8 ml H$_2$O were added and the mixture was cooled with ice. 8.1 g (90 mmol, 1.1 eq.) acryloyl chloride dissolved in 10 ml THF was added drop wise over a period of 30 minutes. The mixture was stirred at room temperature for 3 hours. Subsequently, 1.5 ml of a solution of BHT (10 g/L=45 mmol/L) in ethyl acetate was added. Subsequently, the solvent was evaporated and 100 ml water was added. The mixture was extracted twice with 100 ml isopropyl acetate and then the organic phase has been washed twice with 50 ml 1N sulfuric acid, twice with 50 ml of a saturated NaHCO$_3$ solution and twice with 50 ml, dried over sodium sulfate and evaporated yielding the acrylate in 90% yield.

$^{13}$C NMR (CDCl$_3$; ppm): 166.37/165.85 (C=O), 133.28/133.11 (CH$_2$=CH—CH$_2$), 128.07/127.82 (CH$_2$=CH—CO), 127.75/127.42 (CH$_2$=CH-00), 116.96/116.55 (CH$_2$=CH—CH$_2$), 62.70/62.66 (CH$_2$OH), 50.07/49.59 (CH$_2$=CH—CH$_2$), 47.26/46.57 (N-CH$_2$—CH$_2$), 32.60/32.57 (CH$_2$CH$_2$CH$_2$OH), 29.21/29.17/29 (CH$_2$CH$_2$CH$_2$OH), 27.58/26.79/26.59/25.57/25.55 (CH$_2$).

The above synthetic pathway may be adapted for the preparation of any compound of formula (I) according to the present invention.

Synthesis of N-Acryl-7-allylamino-heptanol 26.5 g (192 mmol, 1.2 eq.) K$_2$CO$_3$ was suspended in 96 ml (1.28 mol, 8 eq.) allyl amine. 31.4 g (160 mmol, 1 eq.) 7-Bromo-heptanol was added dropwise over a period of 60 minutes at 0-4° C. and the mixture was stirred for 20 hours. After filtration and evaporation, the amine was obtained in 99% yield and was used without further purification.

27.6 g (160 mmol, 1 eq.) of the allylamino heptanol were dissolved in 200 ml THF, 20 ml of a 50% NaOH solution in water was added and the mixture was cooled with ice. Subsequently, 15.9 g (176 mmol, 1.1 eq.) acryloyl chloride dissolved in 20 ml THF have been added dropwise over a period of 60 minutes at 0-4° C. The mixture has been stirred for 1 hours at room temperature and then 3 ml of a 40 mM BHT solution in ethylacetate has been added. THF has been removed in vacuum, 200 ml of H$_2$O have been added and the mixture was extracted two times with 150 ml ethylacetate. The organic phase was washed two times with 50 ml of a 1M H$_2$SO$_4$ solution and once with 50 ml of a sat. NaHCO$_3$ solution, dried over Na$_2$SO$_4$ and evaporated yielding 36 g (98%) of the desired product.

Synthesis of N-Acryl-6-allylamino-hexanole 23 g (166 mmol, 1.2 eq.) K$_2$CO$_3$ was suspended in 75 ml (1 mol, 7.2 eq.) allyl amine. 25 g (139 mmol, 1 eq.) 6-Bromo-hexanol was added dropwise over a period of 10 minutes at room temperature and the mixture was stirred for 20 hours. After filtration and evaporation the amine was obtained in 98% yield and was used without further purification.

21 g (134 mmol, 1 eq.) of the allylamino hexanol and 20.4 ml (147 mmol, 1.1 eq.) triethylamine were dissolved in 200 ml dichloromethane and the mixture was cooled with ice. Afterwards 11.9 g (147 mmol, 1.1 eq.) acryloyl chloride dissolved in 20 ml dichloromethane was added dropwise over a period of 20 minutes at 0-4° C. The mixture was stirred for 3 hours at room temperature and then 1 ml of a 40 mM BHT solution in ethyl acetate was added followed by 100 ml of dest. H$_2$O. The organic phase was washed twice with 50 ml 1M H$_2$SO$_4$ and once with 50 ml of a sat. NaHCO$_3$ solution, dried over Na$_2$SO$_4$ and evaporated yielding 20 g (71%) of the desired product.

Synthesis of N-Acryl-10-allylamino-decanole 28 g (202 mmol, 1.2 eq.) K$_2$CO$_3$ was suspended in 75 ml (1 mol, 7.9 eq.) allyl amine. 30 g (126 mmol, 1 eq.) 10-Bromo-decanole was added dropwise over a period of 10 minutes at room temperature and the mixture was stirred for 20 hours. After filtration and evaporation the amine was obtained in 98% yield and was used without further purification.

25 g (117 mmol, 1 eq.) of the allylamino decanol and 17.8 ml (129 mmol, 1.1 eq.) triethylamine were dissolved in 200 ml dichloromethane and the mixture was cooled with ice. Afterwards 11.6 g (129 mmol, 1.1 eq.) acryloyl chloride dissolved in 30 ml dichloromethane was added dropwise over a period of 20 minutes at 0-4° C. The mixture was stirred for 3 hours at room temperature and then 1.5 ml of a 40 mM BHT solution in ethyl acetate was added followed by 100 ml of dest. H$_2$O. The organic phase was washed two times with 50 ml 1M H$_2$SO$_4$ and once with 50 ml of a sat. NaHCO$_3$ solution, dried over Na$_2$SO$_4$ and evaporated yielding 29 g (93%) of the desired product.

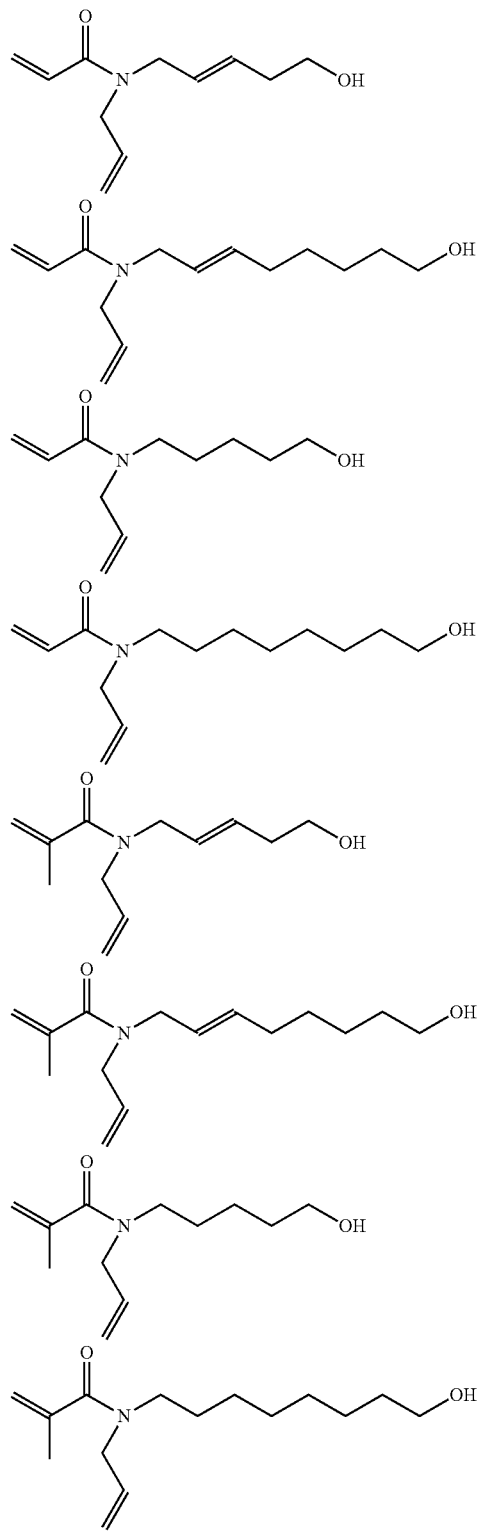

-continued
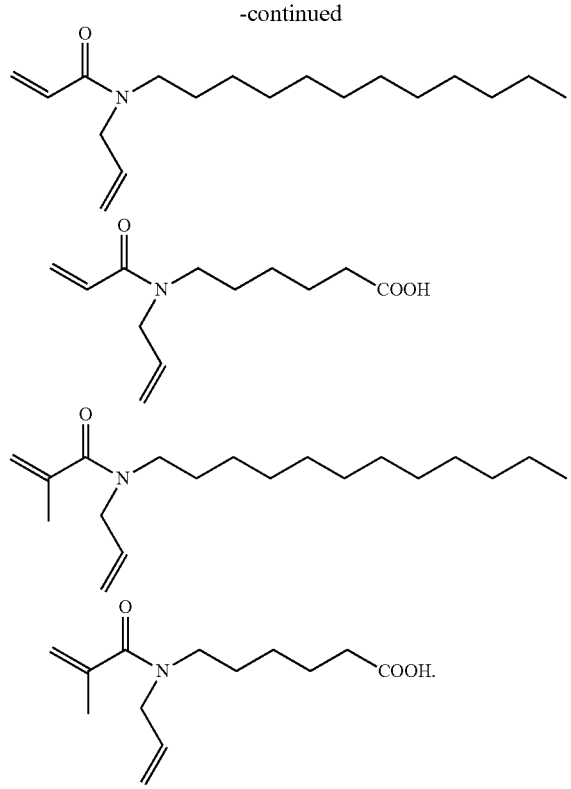

The invention claimed is:

1. A dental composition comprising
(a) a polymerizable compound of the following formula (I):

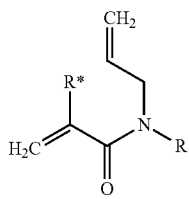

wherein
R represents a straight chain or branched $C_{2-18}$ alkyl or alkenyl group, which may be substituted by a group selected from a hydroxyl group, a $C_{1-4}$ alkoxy group, a tertiary amino group, and a carboxylic acid group, and wherein 1 to 8 carbon atoms in the main chain of the $C_{2-18}$ alkyl or alkenyl group may independently from each other be replaced by a heteroatom selected from an oxygen atom and a sulfur atom, and
R* represents a hydrogen atom or a methyl group; and
(b) a polymerization initiator system.

2. The dental composition according to claim 1, wherein R is a group of the following formula (II)

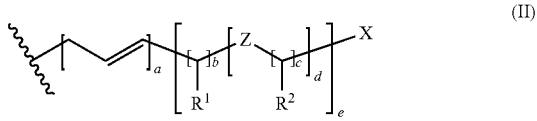

wherein
X is a hydrogen atom, a hydroxyl group, a $C_{1-4}$ alkoxy group, a tertiary amino group or a carboxylic acid group;
Z is an oxygen atom or a sulfur atom, and in case more than one Z is present, the Z may be the same or different;
$R^1$ is a hydrogen atom or a group selected from a hydroxyl group, a $C_{1-4}$ alkyl group, a $C_{1-4}$ alkoxy group, a tertiary amino group, and a carboxylic acid group, and in case more than one group $R^1$ is present, the groups may be the same or different;
$R^2$ is a hydrogen atom or a group selected from a hydroxyl group, a $C_{1-4}$ alkyl group, a $C_{1-4}$ alkoxy group, a tertiary amino group, and a carboxylic acid group, and in case more than one group $R^2$ is present, the groups may be the same or different;
a is 0 or 1;
b is an integer of from 2 to 18;
c is an integer of from 2 to 16;
d is an integer of from 0 to 8; and
e is an integer of from 1 to 3.

3. The dental composition according to claim 1, wherein the polymerizable compound is a compound of the following formula (Ia) or (Ib):

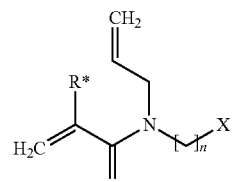

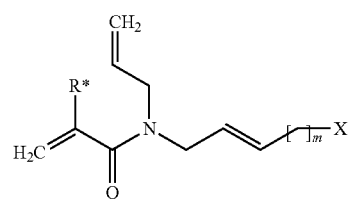

wherein
R* represents a hydrogen atom or a methyl group,
X is a hydroxyl group, a tertiary amino group or a carboxylic acid group;
n is an integer of from 5 to 18, and
m is an integer of from 2 to 15.

4. The dental composition according to claim 3, wherein n in the compound of the following formula (III) is 6 to 12, or wherein m in the compound of the formula (IV) is 2 to 8.

5. The dental composition according to claim 1, wherein the polymerizable compound of the following formula (I) has a dynamic viscosity at 23° C. of at most 10 Pa·s.

6. The dental composition according to claim 2, wherein X is a hydroxyl group or a carboxylic acid group.

7. The dental composition according to claim 1, wherein the compound of formula (I) is contained in an amount of from 1 to 80 percent by weight based on the total weight of the composition.

8. The dental composition according to claim 1, wherein the polymerization initiator is a photoinitiator, a redox initiator, or a mixture thereof.

9. The dental composition according to claim 1, wherein the polymerization initiator is contained in an amount of from 0.01 to 10 percent based on the total weight of the composition.

10. The dental composition according to claim 1, which is selected from a highly filled dental composite, a flowable dental composite, pit and fissure sealant, a dental adhesive, a dental cement, root canal sealer, a glass ionomer cement, and a dental infiltrant.

11. A polymerizable compound of the following formula (I'):

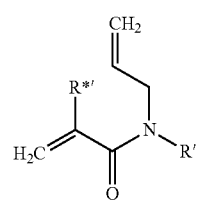

wherein
R' represents a straight chain or branched $C_{5-18}$ alkyl or alkenyl group, which may be substituted by a group selected from a hydroxyl group, a $C_{1-4}$ alkoxy group, a tertiary amino group, and a carboxylic acid group, and wherein 1 to 8 carbon atoms in the main chain of the $C_{5-18}$ alkyl or alkenyl group may independently from each other be replaced by a heteroatom selected from an oxygen atom and a sulfur atom, and R*' represents a hydrogen atom or a methyl group, provided that the compound is not N-allyl-N-tridecylacrylamide, N-allyl-N-(2,5,8,11-tetraoxatridecan-13-yl)acrylamide or N-octyl-N-allylacrylamide.

12. The compound according to claim 11, wherein R' is a group of the following formula (II')

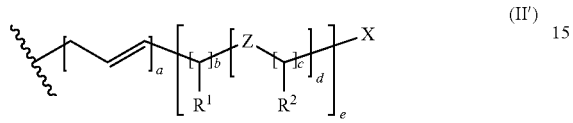

wherein
X is a hydrogen atom, a hydroxyl group, a $C_{1-4}$ alkoxy group, a tertiary amino group or a carboxylic acid group;
Z is an oxygen atom or a sulfur atom, and in case more than one Z' is present, the Z' may be the same or different;
$R^1$ is a hydrogen atom or a group selected from a hydroxyl group, a $C_{1-4}$ alkyl group, a $C_{1-4}$ alkoxy group, a tertiary amino group, and a carboxylic acid group, and in case more than one group $R^{1'}$ is present, the groups may be the same or different;
$R^2$ is a hydrogen atom or a group selected from a hydroxyl group, a $C_{1-4}$ alkyl group, a $C_{1-4}$ alkoxy group, a tertiary amino group, and a carboxylic acid group, and in case more than one group $R^{2'}$ is present, the groups may be the same or different;
a is 0 or 1;
b is an integer of from 2 to 18;
c is an integer of from 2 to 16;
d is an integer of from 0 to 8; and
e is an integer of from 1 to 3,
provided that when a=d=0, then b is at least 5.

13. The compound according to claim 12, which is a compound of the following formula (III') or (IV'):

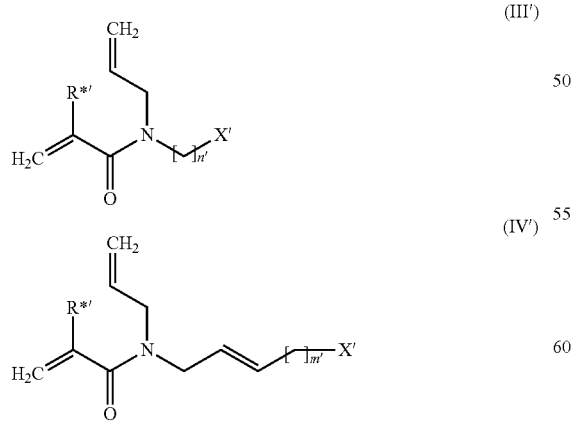

wherein
R*' represents a hydrogen atom or a methyl group, preferably a hydrogen atom, X' is a hydrogen atom, a hydroxyl group, a tertiary amino group or a carboxylic acid group;
n' is an integer of from 5 to 18, and
m' is an integer of from 2 to 15.

14. The compound according to claim 13, which is selected from the following compounds: